(12) United States Patent
Seto et al.

(10) Patent No.: US 10,359,330 B2
(45) Date of Patent: Jul. 23, 2019

(54) PRESSURE SENSOR

(71) Applicant: Azbil Corporation, Tokyo (JP)

(72) Inventors: Yuki Seto, Tokyo (JP); Yoshiyuki Ishikura, Tokyo (JP); Rina Ogasawara, Tokyo (JP)

(73) Assignee: Azbil Corporation, Tokyo (JP)

( * ) Notice: Subject to any disclaimer, the term of this patent is extended or adjusted under 35 U.S.C. 154(b) by 179 days.

(21) Appl. No.: 15/638,782

(22) Filed: Jun. 30, 2017

(65) Prior Publication Data
US 2018/0010976 A1 Jan. 11, 2018

(30) Foreign Application Priority Data

Jul. 8, 2016 (JP) .................................. 2016-135895

(51) Int. Cl.
*G01L 9/00* (2006.01)
*G01L 13/02* (2006.01)
*G01L 19/14* (2006.01)

(52) U.S. Cl.
CPC .......... *G01L 9/0055* (2013.01); *G01L 9/0051* (2013.01); *G01L 9/0052* (2013.01);
(Continued)

(58) Field of Classification Search
CPC ... G01L 9/0051; G01L 9/0052; G01L 9/0055; G01L 13/025; G01L 19/147; A61B 2562/0247
See application file for complete search history.

(56) References Cited

U.S. PATENT DOCUMENTS 3,624,714 A * 11/1971 Frassrand ............. G01L 9/0055
338/4
4,680,569 A * 7/1987 Yamaki ............... G01L 19/0084
338/36
(Continued)

FOREIGN PATENT DOCUMENTS

| CN | 108463704 A | 8/2018 |
|---|---|---|
| JP | S63217671 A | 9/1988 |
| JP | 2004045140 A | 2/2004 |

OTHER PUBLICATIONS

European Patent Office, "Extended European Search Report," issued in European Patent Application No. 17 180 256.4, which is a European Counterpart of U.S. Appl. No. 15/638,782 dated Nov. 21, 2017, 8 page.

(Continued)

*Primary Examiner* — David J Bolduc
(74) *Attorney, Agent, or Firm* — Amster, Rothstein & Ebenstein LLP

(57) ABSTRACT

A pressure sensor includes a diaphragm having a first principal surface and a second principal surface, a semiconductor chip in which resistors constituting a strain gauge are formed, a first structural body having one end coupled to a center of a second principal surface of the diaphragm and the other end coupled to the other surface of the semiconductor chip, and at least two second structural bodies disposed in two straight lines, orthogonal to each other, that pass through the center of the diaphragm in plan view so as to be disposed separately from the first structural body, and having one ends coupled to the second principal surface and the other ends coupled to the other surface of the semiconductor chip, in which the resistors are formed in regions between the first structural body and the second structural bodies in plan view in the semiconductor chip.

18 Claims, 23 Drawing Sheets

(52) U.S. Cl.
    CPC .... *G01L 13/025* (2013.01); *A61B 2562/0247* (2013.01); *G01L 19/147* (2013.01)

(56) References Cited

U.S. PATENT DOCUMENTS

| | | | | |
|---|---|---|---|---|
| 4,926,155 | A | * | 5/1990 | Colla .................. G01L 19/0645 338/36 |
| 2007/0277616 | A1 | | 12/2007 | Nikkel et al. |
| 2015/0338293 | A1 | * | 11/2015 | Masunishi ................ G01L 1/22 73/649 |
| 2018/0136062 | A1 | * | 5/2018 | Zheng ................... G01L 9/0051 |
| 2019/0025144 | A1 | | 1/2019 | Seto et al. |

OTHER PUBLICATIONS

The State Intellectual Property Office of People's Republic of China, "First Office Action", issued in Chinese Patent Application No. 201710548007.0, which is a counterpart to U.S. Appl. No. 15/638,782, dated Mar. 25, 2019, 13 pages (6 pages of English Translation of Office Action and 7 pages of Original Chinese Office Action).

* cited by examiner

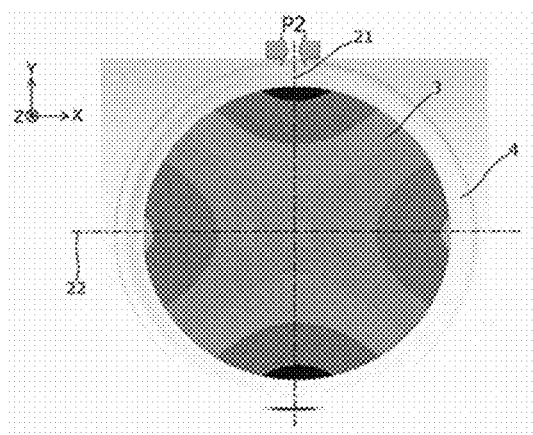
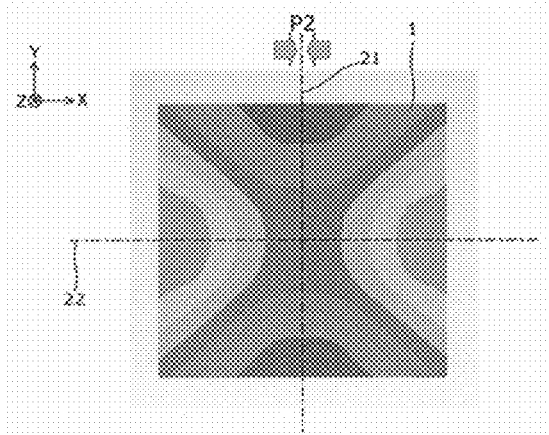
Fig.11A    Fig.11B
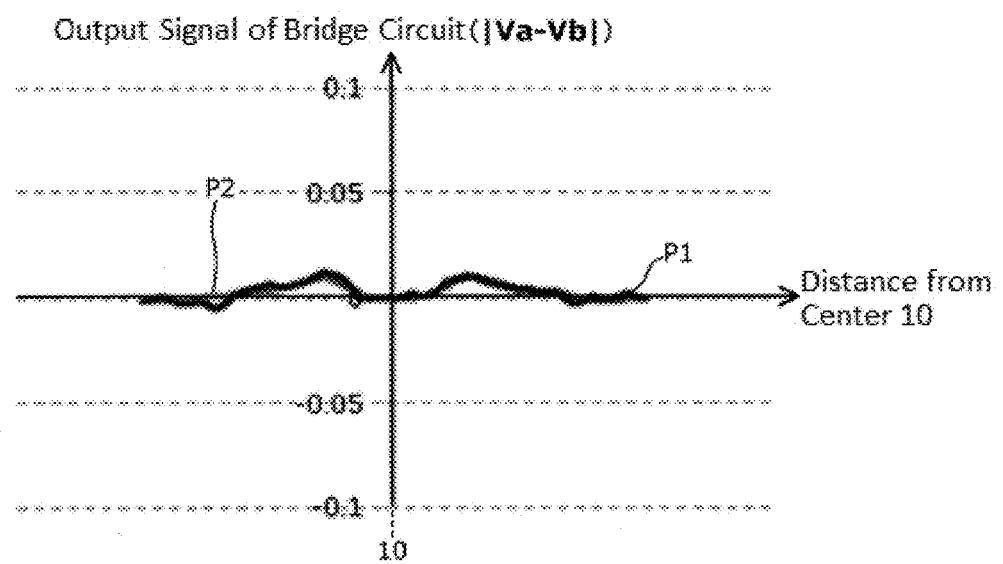
Fig.12

PRESSURE SENSOR

CROSS-REFERENCE TO RELATED APPLICATIONS

The present application claims the benefit of and priority to Japanese Patent Application No. 2016-135895, filed on Jul. 8, 2016, the entire contents of which are incorporated by reference herein.

TECHNICAL FIELD

The present invention relates to a pressure sensor and, for example, to a sanitary pressure sensor.

BACKGROUND ART

Generally, it is necessary to meet strict conditions, such as corrosive resistance, cleanness, reliability, and versatility, for a pressure sensor for detecting the pressure of a fluid to be permitted as a sanitary pressure sensor that needs consideration to sanitation used in production sites for food, drugs, and the like.

For example, to ensure corrosive resistance, a sanitary pressure sensor needs to include a material having high corrosive resistance, such as stainless steel (SUS), ceramic, or titanium in the wetted part in contact with a measurement target fluid (for example, liquid) for which the pressure is measured. In addition, to ensure cleanness, a sanitary pressure sensor needs to have a flash diaphragm structure that enables easy cleaning and high heat and impact resistance against steam cleaning. In addition, to ensure reliability, a sanitary pressure sensor needs to have a structure (oil free structure) that does not include encapsulant and a structure (high rigidity barrier) that makes it difficult to break a diaphragm.

Since materials and structures that can be used for a sanitary pressure sensor are restricted as compared with other pressure sensors as described above, it is difficult to improve sensor sensitivity. For example, to achieve a structure that makes it difficult to break a diaphragm, although the film thickness of the diaphragm needs to be increased (the aspect ratio of the diameter to the thickness of the diaphragm needs to be reduced), increase in the thickness of a diaphragm generally reduces the sensor sensitivity because the amount of deformation of a diaphragm becomes minute. Accordingly, a technique for accurately detecting minute deformation of a diaphragm is necessary for a sanitary pressure sensor.

For example, PTL 1 and PTL 2 disclose load conversion type pressure sensors that improve the sensitivity of the sensors by transmitting the displacement of only the center part of a diaphragm to a semiconductor chip (beam member) of Si or the like on which a strain gauge including diffusion resistors is formed and detecting changes in the resistance value of the diffusion resistors caused by the piezoresistive effect based on distortion of the semiconductor chip.

Specifically, in the conventional load conversion type pressure sensor disclosed in PTL 1 and PTL 2, the center part of a semiconductor chip that is rectangular in plan view is supported by the center part of a diaphragm and both ends of the semiconductor chip are fixed at a position that does not move substantially. For example, in PTL 1, the center of a strip semiconductor chip is supported by a rod-shaped member called a pivot at the center of the diaphragm and both ends in the longitudinal direction of the semiconductor chip are fixed to the thick-walled part formed at the outer peripheral edge of the diaphragm via an insulating base. In addition, in PTL 2, the center of a rectangular semiconductor chip is fixed to the center of a diaphragm and the both ends in the longitudinal direction of a semiconductor chip are fixed to a seat that does not move.

CITATION LIST

Patent Literature

[PTL 1] JP-A-2004-45140
[PTL 2] JP-A-63-217671

SUMMARY OF THE INVENTION

Generally, a sanitary pressure sensor has a joint (for example, a ferrule joint) in a connection part with a pipe through which a measurement target fluid flows.

Connection between the pipe and the sanitary pressure sensor is made using a connection member called a clamp band (also referred to below as a "clamp" simply) as illustrated in FIG. 40. Specifically, as illustrated in FIG. 41, the joint for a pipe 200 and the joint for a sanitary pressure sensor 300 are disposed so as to face each other, the two joints are clamped by semicircular fixing portions 51A and 51B of a clamp 50, and the fixing portions 51A and 51B are tightened by a nut 52, thereby making connection between the pipe 200 and the sanitary pressure sensor 300.

However, when connection between the pipe and the sanitary pressure sensor is made by the clamp, the diaphragm of the sanitary pressure sensor is deformed to no small extent and the resistance values of resistors included in a strain gauge are changed, possibly shifting the zero point (offset) of a sensor output. In the case of the pressure sensor having a semiconductor chip that is rectangular in plan view as disclosed in PTL 1 and PTL 2 above, since the deviation amounts of the resistance values of the resistors included in the strain gauge are changed depending on the position of the nut for tightening the clamp, the shift amount of the zero point varies depending on the position at which the clamp is fixed. Accordingly, in such a pressure sensor, to compensate for the zero point of a sensor output, it is necessary to change the correction amount of the zero point according to the position at which the clamp is tightened or instruct the user to the position at which the clamp is tightened in advance.

The invention addresses the above problems with an object of suppressing variations in the shift amount of the zero point of a sensor output when a pipe through which a measurement target fluid flows is connected to a pressure sensor via a clamp.

A pressure sensor (100, 100A, 100B, 100C, 100D, 101, 101A, 102, 102A, 103, 103A) according to the invention includes a diaphragm (3) having a first principal surface (3A) receiving a pressure of a measurement target fluid and a second principal surface (3B) opposite to the first principal surface, a semiconductor chip (1) having a plurality of resistors (R1 to R4) on one surface thereof, the resistors being included in a strain gauge, a first structural body (2a) provided orthogonally so that one end thereof is coupled to a center (30) of the second principal surface of the diaphragm and the other end is coupled to the other surface of the semiconductor chip, and at least two second structural bodies (2b to 2e) having one ends coupled to the second principal surface and the other ends coupled to the other surface of the semiconductor chip, the at least two second structural bodies being disposed in two straight lines (21, 22)

that pass through the center of the second principal surface of the diaphragm and are orthogonal to each other in plan view, the at least two second structural bodies being disposed separately from the first structural body, in which the resistors are formed in regions between the first structural body and the second structural bodies in plan view.

In the pressure sensor (100), preferably, the semiconductor chip is formed in a square in plan view, the other end of the first structural body is coupled to a center (10) of the other surface of the semiconductor chip, and each of the other ends of the second structural bodies is coupled to the other surface of the semiconductor chip along each of the sides of the other surface of the semiconductor chip.

In the pressure sensor (101), preferably, the plurality of resistors are included in a bridge circuit (16), a first resistor (R1) and a second resistor (R2) included in one of two pairs of resistors connected in parallel between two output terminals of the bridge circuit are formed in a region between a coupling surface of one of the second structural bodies disposed in one straight line (21) of the two straight lines and a coupling surface of the first structural body in plan view in the semiconductor chip and a third resistor (R3) and a fourth resistor (R4) included in the other of the two pairs of resistors are formed in a region between a coupling surface of another of the second structural bodies disposed in the other straight line (22) of the two straight lines and the coupling surface of the first structural body in plan view in the semiconductor chip, the first resistor and the fourth resistor extend in the same direction in plan view, and the second resistor and the third resistor extend in the same direction in plan view.

In the pressure sensor, preferably, a direction in which the first resistor and the fourth resistor extend is orthogonal to a direction in which the second resistor and the third resistor extend in plan view.

In the pressure sensor (100A), preferably, the plurality of resistors include four resistors constituting a bridge circuit and the four resistors extend in the same direction in plan view and each of the four resistors is formed in a region between a coupling surface of the first structural body and a coupling surface of each of the second structural bodies in the semiconductor chip.

In the pressure sensor (101, 101A), preferably, the semiconductor chip (1a) is formed in a cross in plan view, the other end of the first structural body is coupled to the center of the other surface of the semiconductor chip, and each of the other ends of the second structural bodies is coupled to each of four arms on the other surface of the semiconductor chip.

In the pressure sensor (101), preferably, the plurality of resistors are included in a bridge circuit (16), a first resistor (R1) and a second resistor (R2) included in one of two pairs of resistors connected in parallel between two output terminals of the bridge circuit are formed in a region between a coupling surface of one of the second structural bodies disposed in one straight line (21) of two straight lines and a coupling surface of the first structural body in plan view in the semiconductor chip and a third resistor (R3) and a fourth resistor (R4) included in the other of the two pairs of resistors are formed in a region between a coupling surface of another of the second structural bodies disposed in the other straight line (22) of the two straight lines and the coupling surface of the first structural body in plan view in the semiconductor chip, the first resistor and the fourth resistor extend in the same direction in plan view, and the second resistor and the third resistor extend in the same direction in plan view.

In the pressure sensor (101), preferably, the direction in which the first resistor and the fourth resistor extend is orthogonal to the direction in which the second resistor and the third resistor extend in plan view.

In the pressure sensor (101A), preferably, the plurality of resistors include four resistors constituting a bridge circuit and the four resistors extend in the same direction in plan view and each of the four resistors is formed in a region between a coupling surface of the first structural body and a coupling surface of each of the second structural bodies in the semiconductor chip.

In the pressure sensor (102, 102A), preferably, the at least two second structural bodies (2b, 2c) are two second structural bodies, the semiconductor chip is formed in a polygon in plan view, the other end of the first structural body (2a) is coupled to a region including one corner of the other surface of the semiconductor chip, the other end of one second structural body (2b) of the second structural bodies is coupled along one side (12) of two sides forming the one corner of the other surface of the semiconductor chip, the other end of the other second structural body (2c) of the second structural bodies is coupled along the other side (13) of the two sides forming the one corner of the other surface of the semiconductor chip, the plurality of resistors are included in a bridge circuit (16), a first resistor (R1) and a second resistor (R2) included in one of two pairs of resistors connected in parallel between two output terminals of the bridge circuit are formed in a region between a coupling surface of the first structural body and a coupling surface of the one of the second structural bodies in plan view in the semiconductor chip and a third resistor (R3) and a fourth resistor (R4) included in the other of the two pairs of resistors are formed in a region between the coupling surface of the first structural body and the coupling surface of the other of the second structural bodies in plan view in the semiconductor chip, the first resistor and the fourth resistor extend in the same direction in plan view, and the second resistor and the third resistor extend in the same direction in plan view.

In the pressure sensor (102), preferably, the direction in which the first resistor and the fourth resistor extend is orthogonal to the direction in which the second resistor and the third resistor extend in plan view.

In the pressure sensor (102A), preferably, an inner angle of one corner to which the first structural body or the second structural bodies is not coupled is larger than 180 degrees in the semiconductor chip (1c).

In the pressure sensor (103, 103A), preferably, the semiconductor chip is formed in a square in plan view, the plurality of resistors (R1 to R4) includes four resistors constituting a bridge circuit (16), the other end of the first structural body is coupled to the center of the other surface of the semiconductor chip, the other ends of the second structural bodies are coupled to four corners of the other surface of the semiconductor chip (1d), and the four resistors extend in the same direction in plan view and each of the four resistors is formed in a region between a coupling surface of the first structural body and each of coupling surfaces of the second structural bodies in the semiconductor chip.

In the pressure sensor, preferably, the plurality of resistors is disposed equidistantly from the center (20) of the first structural body in plan view.

In the pressure sensor, preferably, the semiconductor chip has a thin-walled portion (1C) thinner than a portion to which the first structural body and the second structural bodies are coupled and the plurality of resistors is formed in a region on the one surface of the semiconductor chip, the region corresponding to the thin-walled portion.

It should be noted that reference numerals in the drawings corresponding to components of the invention are enclosed in parentheses in the above description.

As described above, according to the invention, it is possible to suppress variations in the shift amount of the zero point of a sensor output when a pipe through which a measurement target fluid flows is connected to a pressure sensor connected via a clamp.

BRIEF DESCRIPTION OF THE DRAWINGS

FIG. 11A is a contour diagram illustrating the displacement in the Z axis direction of the diaphragm 3 when the nut 52 of the clamp 50 is fixed at position P2 illustrated in FIG. 9.

FIG. 11B is a contour diagram illustrating the displacement in the Z axis direction of the semiconductor chip 1 when the nut 52 of the clamp 50 is fixed at position P2 illustrated in FIG. 9.

FIG. 12 illustrates the result of simulation of a sensor output from the pressure sensor according to embodiment 1.

DETAILED DESCRIPTION

Figure 1:
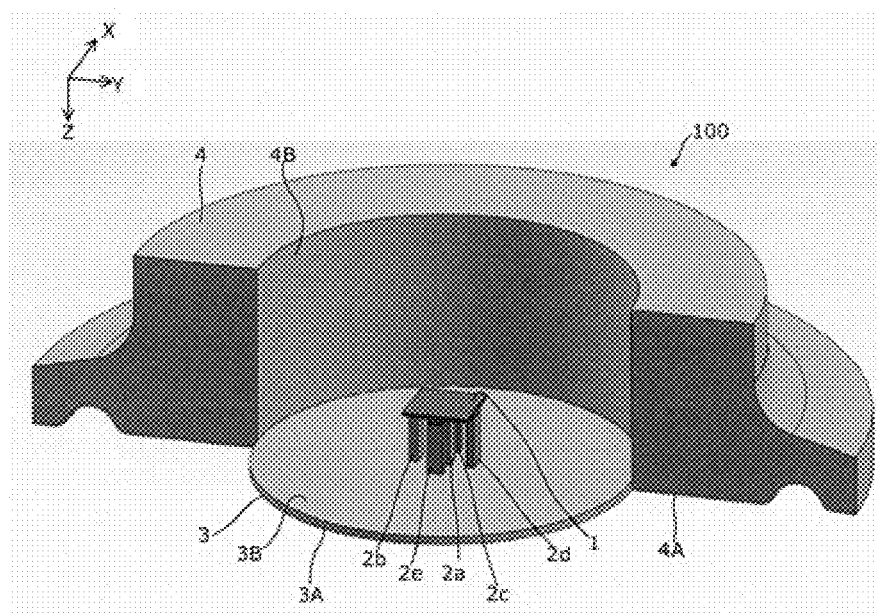
FIG. 1 is a perspective view illustrating the structure of a pressure sensor according to embodiment 1.

Embodiments of the present invention will be described below with reference to the drawings. It should be noted that components common to the individual embodiments are given the same reference numerals to omit repeated descriptions.

Embodiment 1

Figure 2:
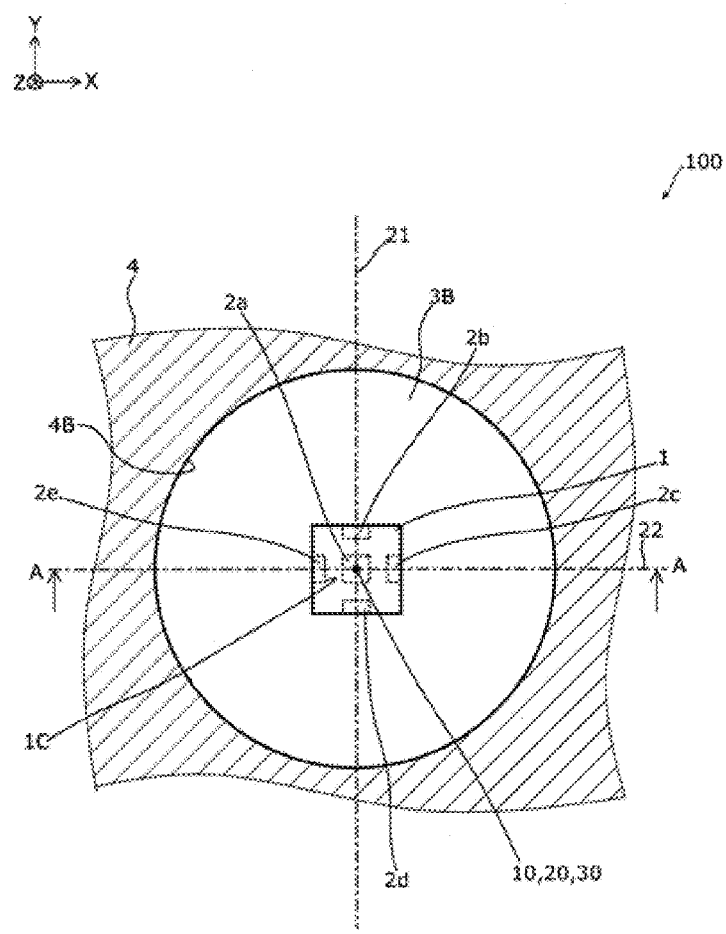
FIG. 2 is a plan view illustrating the structure of the pressure sensor according to embodiment 1.
Figure 3:
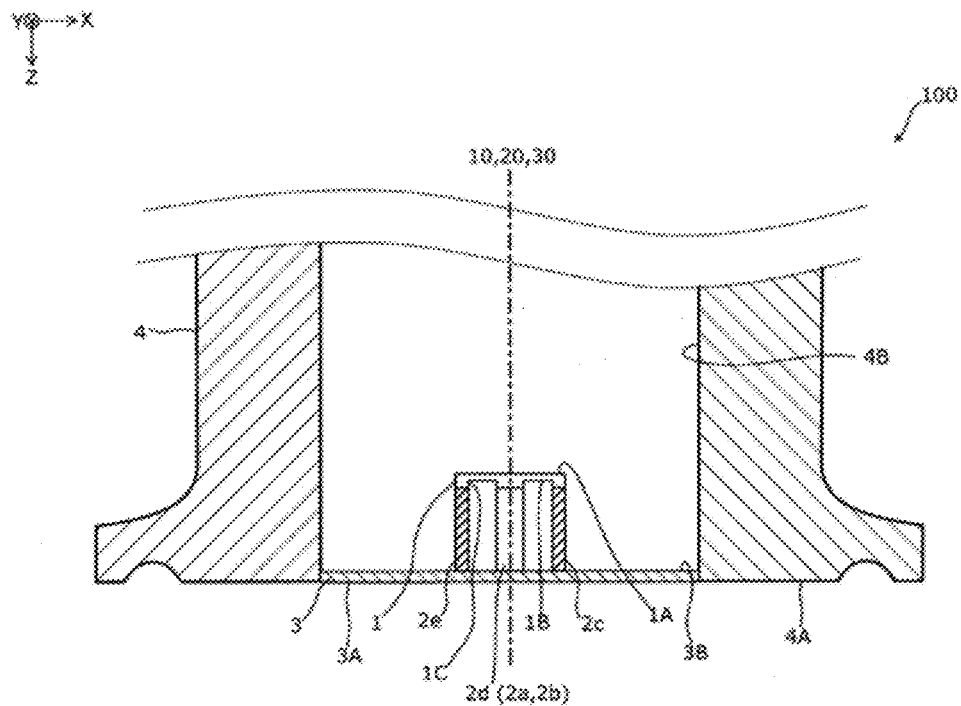
FIG. 3 is a cross-sectional view illustrating the structure of the pressure sensor according to embodiment 1.

FIGS. 1 to 3 illustrate the structure of a pressure sensor according to embodiment 1.

FIG. 1 is a perspective view illustrating a pressure sensor 100 according to embodiment 1, FIG. 2 illustrates the planar structure of the pressure sensor 100 seen from the Z direction in FIG. 1, and FIG. 3 illustrates the cross-sectional structure of the pressure sensor 100 taken along line A-A in FIG. 2. It should be noted that a cross-sectional structure along the axial line 21 is illustrated only for a cylindrical housing 4 in FIG. 1.

The pressure sensor 100 illustrated in FIGS. 1 to 3 is an apparatus that detects a pressure of a measurement target fluid by transmitting, to a semiconductor chip in which a strain gauge is formed, the displacement of a diaphragm when the diaphragm is bent by the pressure of the fluid.

Specifically, the pressure sensor 100 includes a diaphragm 3, a plurality of columnar supporting members 2a, 2b, 2c, 2d, and 2e provided orthogonally to one surface of the diaphragm 3, a semiconductor chip 1 supported by the supporting members 2a to 2e, and the housing 4 for accommodating the diaphragm 3, the supporting members 2a to 2e, and the semiconductor chip 1. Although not illustrated, the pressure sensor 100 may further include a displaying portion (for example, a liquid crystal display) or the like for indicating various types of information, such as the detected pressure value, to the user.

Although FIGS. 1 to 3 illustrate a mechanism for transmitting the bending of the diaphragm 3 in the pressure sensor 100 to the semiconductor chip 1, they do not illustrate other functional portions, such as a circuit for processing signals output from the semiconductor chip 1.

In addition, the directions that are orthogonal to each other and parallel to the planar direction of the diaphragm 3 may be referred to as the X axis direction and the Y axis direction and the direction orthogonal to the planar direction (X axis and Y axis) of the diaphragm 3 may be referred to as the Z axis direction.

The semiconductor chip 1, the diaphragm 3, and the supporting members 2a to 2e are accommodated in the housing 4. The housing 4 is made of a metal material having high corrosive resistance and formed in a cylinder as illustrated in FIGS. 1 to 3, and one end portion 4A thereof is shaped like a joint to be connected to a pipe through which the measurement target fluid flows. The housing 4 is filled with, for example, air and the pressure close to an inner wall 4B is, for example, the atmospheric pressure.

The diaphragm 3 is a film that receives the pressure of the measurement target fluid. The diaphragm 3 is a thin film made of a material having high corrosive resistance, such as, for example, stainless steel (SUS), ceramic, or titanium, and is formed in, for example, a circle in plan view.

The diaphragm 3 is fixed to the part of the housing 4 close to the end portion 4A and blocks the opening part of the end portion 4A of the housing 4. For example, the outer peripheral edge of the diaphragm 3 is coupled to the part of the inner wall 4B of the housing 4 close to the end portion 4A without a gap.

One surface of the diaphragm 3 acts as a pressure receiving surface (wetted surface) 3A in contact with the measurement target fluid and the other surface acts as a supporting surface 3B for supporting the semiconductor chip 1 via the supporting members 2a to 2e. The diaphragm 3 is bent according to the pressure difference between the pressure applied from the measurement target fluid to the pressure receiving surface 3A and the pressure (for example, the atmospheric pressure) applied to the supporting surface 3B.

It should be noted that the diaphragm 3 and the housing 4 of the pressure sensor may not be illustrated in some of the drawings for convenience of description in the drawings of the application.

The semiconductor chip 1 is formed in a polygon in plan view and includes a circuit board made of a semiconductor material, such as Si, and a strain gauge that has resistive elements formed in the circuit board by a known semiconductor manufacturing technique and that detects a strain generated in the semiconductor chip 1 as changes in the resistance values of the above resistive elements.

In the semiconductor chip 1, one surface on which the strain gauge is formed may be referred to below as the "principal surface 1A" and the surface opposite to the principal surface 1A may be referred to below as the "back surface 1B".

It is assumed that the semiconductor chip 1 is formed in a square in plan view as an example in embodiment 1. The above strain gauge will be described in detail later.

Figure 4:
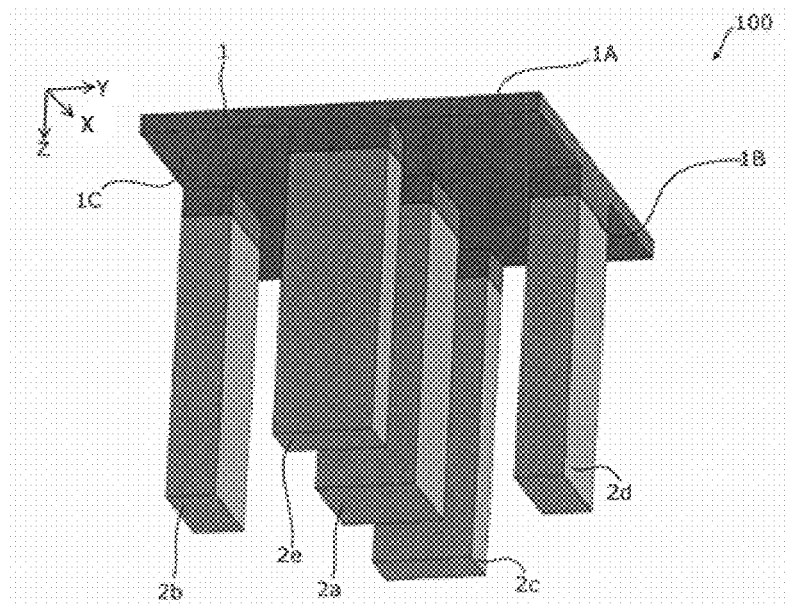
FIG. 4 is a perspective view illustrating a semiconductor chip of the pressure sensor according to embodiment 1 seen from a back surface.

FIG. 4 is a perspective view illustrating a semiconductor chip of the pressure sensor according to embodiment 1 seen from the back surface.

As illustrated in FIG. 4, the part to which the supporting members 2a to 2e are coupled and a thin-walled portion (countersink) 1C, which is thinner than this part, are formed in the surface of the semiconductor chip 1 facing the diaphragm 3 (that is, the back surface 1B of the semiconductor chip 1).

The thin-walled portion 1C can be formed by selectively cutting down the semiconductor chip 1 from the back surface 1B using, for example, a known etching technique.

The supporting members 2a to 2e are structural bodies functioning as columns supporting the semiconductor chip 1 on the diaphragm 3. The supporting members 2a to 2e are formed in, for example, rectangular columns (for example, square columns). In addition, the supporting members 2a to 2e are made of an electrically insulated material. More preferably, the supporting members 2a to 2e are made of a material that is electrically insulated, has certain rigidity, and has smaller thermal conductivity. Glass (for example, borosilicate glass (Pyrex (registered trademark))) can be used as a material of the supporting members 2a to 2e.

The supporting members 2a to 2e have one ends coupled to the supporting surface 3B of the diaphragm 3 and the other ends coupled to the back surface 1B of the semiconductor chip 1.

One end of the supporting member 2a as a first structural body is coupled to the region on the supporting surface 3B that is deformed when a pressure larger than in the supporting surface 3B is applied to the pressure receiving surface 3A and the diaphragm 3 is bent.

More preferably, as illustrated in FIGS. 1 to 3, the supporting member 2a is provided orthogonally so that the one end thereof is coupled to a center 30 of the supporting surface 3B of the diaphragm 3 in plan view and the other end thereof is coupled to a position near a center 10 of the back surface 1B of the semiconductor chip 1 in plan view. In this case, in the supporting member 2a, a center 20 of the supporting member 2a coincides with the center 30 of the diaphragm and the center 10 of the semiconductor chip 1 in plan view.

As illustrated in FIGS. 1 to 3, the supporting members 2b to 2e as second structural bodies are provided separately from the supporting member 2a in straight lines 21 and 22, orthogonal to each other, that pass through the center 20 of the supporting member 2a in plan view.

In the embodiment, the other ends of the supporting members 2b to 2e are coupled to positions near the middle points of the sides of the semiconductor chip 1 that is square in plan view along the sides of the back surface 1B of the semiconductor chip 1.

The heights (lengths in the Z axis direction) of the supporting members 2a to 2e provided orthogonally to the diaphragm 3 are identical to each other. The principal surface 1A of the semiconductor chip 1 supported by the supporting members 2a to 2e is parallel to the supporting surface 3B of the diaphragm 3.

Next, the principle of operation of the pressure sensor 100 according to embodiment 1 will be described in detail.

In the pressure sensor 100, when a pressure larger than the pressure (atmospheric pressure) applied to the supporting surface 3B is applied to the pressure receiving surface 3A of the diaphragm 3, the diaphragm 3 is bent. Since the supporting member 2a is fixed to the center 30 of the diaphragm 3 at this time, the supporting member 2a is displaced greatly in the Z axis direction and is hardly displaced in the X axis direction or in the Y axis direction.

In contrast, since the supporting members 2b to 2e are fixed substantially orthogonally to the supporting surface 3B in positions away from the center 30 of the diaphragm 3, the supporting members 2b to 2e are inclined with respect to the Z axis. That is, the supporting members 2b to 2e are displaced in the X axis direction and the Y axis direction in addition to in the Z axis direction. More specifically, the supporting member 2b to 2e are inclined in a direction (direction toward the inner wall 4B of the housing 4) away from the center 30 (supporting member 2a) of the diaphragm 3.

This pulls the semiconductor chip 1 outward and a bending stress is generated in the semiconductor chip 1. That is, a tensile stress corresponding to mainly the displacement difference in the Z axis direction between the supporting member 2a and the supporting members 2b to 2e is generated in the part inside the semiconductor chip 1 close to the principal surface 1A and a tensile stress corresponding to the displacement difference in the X axis direction and a tensile stress corresponding to the displacement difference in the Y axis direction are also generated. Accordingly, if resistors R1 to R4 included in the above strain gauge (bridge circuit) are formed appropriately in the region in the semiconductor chip 1 in which the above tensile stress is generated, it is possible to detect the pressure of the measurement target fluid highly accurately.

Next, the strain gauge of the semiconductor chip 1 will be specifically described.

Figure 5:
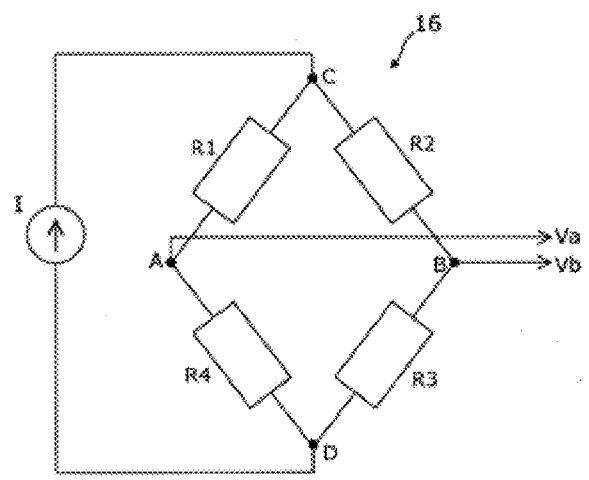
FIG. 5 illustrates the structure of a bridge circuit as a strain gauge.

As illustrated in FIG. 5, the strain gauge described above includes a bridge circuit 16 having the four resistors (for example, diffusion resistors) R1 to R4 formed on, for example, the principal surface 1A of the semiconductor chip 1. The pressure sensor 100 can measure the pressure of the measurement target fluid by detecting changes in the resistance values of the resistors R1 to R4 as changes in voltages caused by the stresses generated in the semiconductor chip 1 when the diaphragm 3 is bent in the state in which a constant current flows through the bridge circuit 16.

Figure 6:
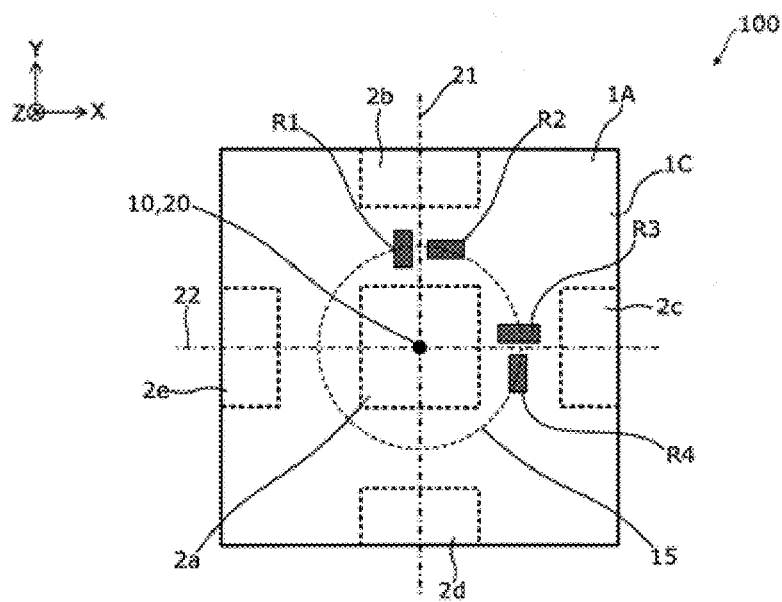
FIG. 6 illustrates an example of disposing resistors on the semiconductor chip in the pressure sensor according to embodiment 1.

FIG. 6 illustrates an example of disposing the resistors R1 to R4 on the semiconductor chip 1 in the pressure sensor according to embodiment 1.

The resistors R1 and R4 are formed in the region (that is, the region on the principal surface 1A (on which the resistor R1 to R4 are formed) of the semiconductor chip 1 in which a tensile stress is generated) in which a stress generated in the semiconductor chip 1 is positive (+) when the diaphragm 3 is bent by the pressure of the fluid. Specifically, as illustrated in FIG. 6, the resistors R1 to R4 are formed in the region on the principal surface 1A corresponding to the thin-walled portion 1C. Of these resistors, the resistors R1 and R2 are formed in the region between the coupling surface of the supporting member 2b and the coupling surface of the supporting member 2a disposed in the straight line 21 in plan view. In addition, the resistors R3 and R4 are formed in the region between the coupling surface of the supporting member 2c and the coupling surface of the supporting member 2a disposed in the straight line 22 in plan view.

The resistors R1 to R4 are formed in, for example, rectangles (strips) in plan view. Although the resistors R1 to R4 are formed in the same shape in plan view and have the same resistance value in the embodiment, the invention is not limited to this embodiment.

The resistor R1 and the resistor R2 may extend in directions different from each other in plan view and the resistor R3 and the resistor R4 may extend in directions different from each other in plan view. The direction in which the resistors R1 to R4 extend refers to the direction in which a current flows when a voltage is applied to the resistors R1 to R4.

As illustrated in FIG. 6, the resistor R1 and the resistor R4 may extend in the same direction in plan view and the resistor R2 and the resistor R3 may extend in the same direction in plan view. Additionally, the direction in which the resistor R1 and the resistor R4 extend may be orthogonal to the direction in which the resistor R2 and the resistor R3 extend. For example, as illustrated in FIG. 6, the resistor R1 and the resistor R4 may extend in the direction parallel to the straight line 21 and the resistor R2 and the resistor R3 may extend in the direction parallel to the straight line 22.

In addition, the resistors R1 to R4 may be disposed equidistantly (within a deviation of, for example, plus or minus 10 percent) from the center 20 of the supporting member 2a. Specifically, the distances from the center 10 of the semiconductor chip 1 to the centers of the rectangular resistors R1, R2, R3, and R4 may be the same. For example, as illustrated in FIG. 6, the resistor R1, R2, R3, and R4 may be disposed in the circumference of a circle 15 having the same center as the semiconductor chip 1 in plan view. The diameter of the circle 15 is not particularly limited as long as the circle 15 fits within the thin-walled portion 1C.

The pressure sensor 100 configured as described above has the following effects. The effects of the pressure sensor 100 will be described below by comparing the pressure sensor 100 according to embodiment 1 with a different pressure sensor 901.

First, the pressure sensor 901, which is a comparative example for the pressure sensor 100 according to embodiment 1, will be described.

Figure 7:
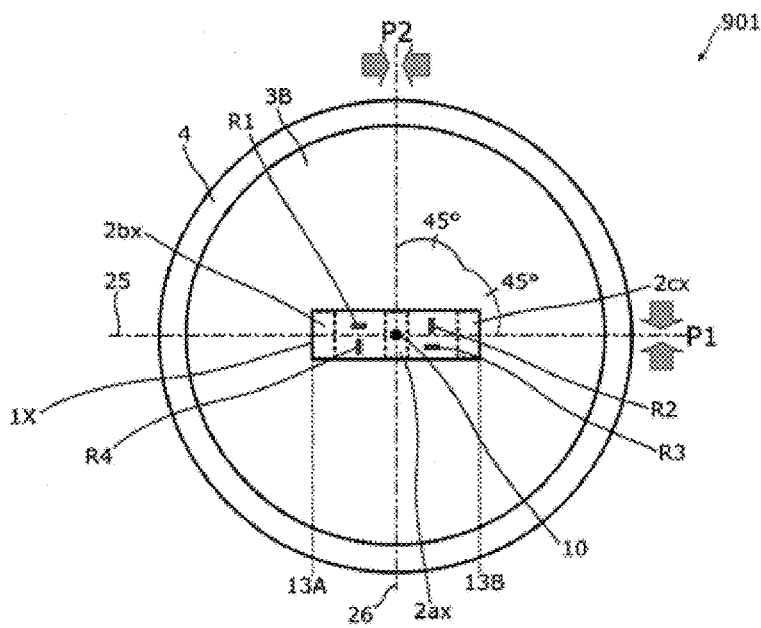
FIG. 7 illustrates a pressure sensor 901 in which a semiconductor chip 1X that is rectangular in plan view is supported by supporting members 2ax, 2bx, and 2cx at a position close to a center 30 of a supporting surface 3B of a diaphragm 3 as a comparative example for pressure sensor 100.

FIG. 7 illustrates the pressure sensor 901 as the comparative example.

The pressure sensor 901 has a semiconductor chip 1X that is rectangular in plan view and three supporting members 2ax, 2bx, and 2cx for supporting the semiconductor chip 1X provided side by side orthogonally in a straight line 25 passing through the center 30 of the supporting surface 3B of the diaphragm 3.

Figure 8:
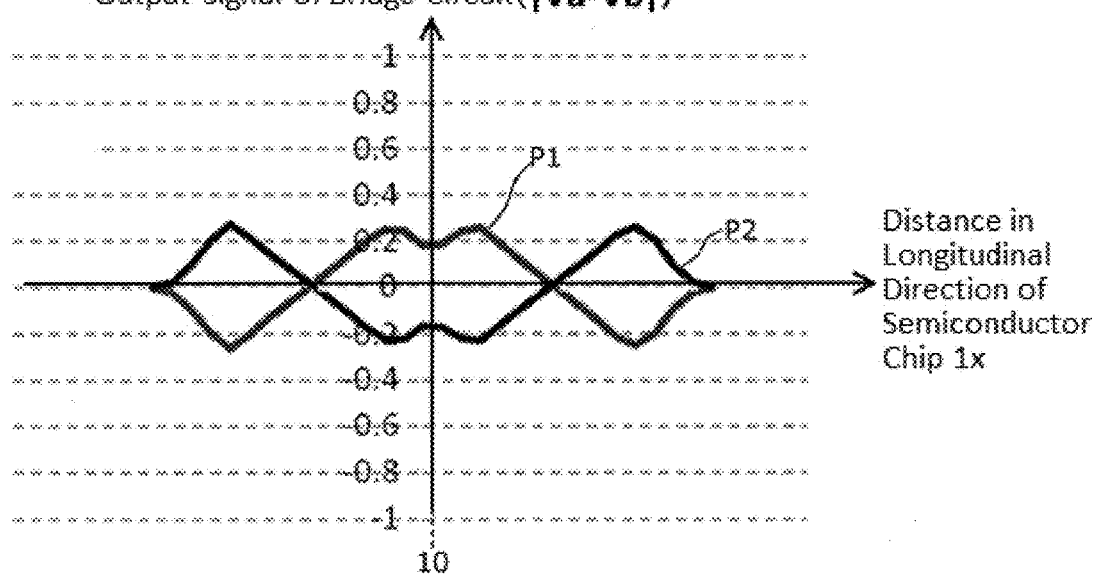
FIG. 8 illustrates the result of simulation of a sensor output from the pressure sensor 901 in FIG. 7 using the finite element method.

FIG. 8 illustrates the result of simulation of a sensor output (an output signal of the bridge circuit) of the above pressure sensor 901 using the finite element method (FEM). In FIG. 8, the horizontal axis represents the distance in the longitudinal direction of the semiconductor chip 1X from the center in the longitudinal direction of the semiconductor chip 1X when the center is assumed to be 0 and the vertical axis represents the magnitude of an output signal (|Va−Vb|) of the bridge circuit 16 obtained by conversion based on the stress distribution of the four resistors R1 to R4 of the semiconductor chip 1X.

In FIG. 8, reference numeral P1 represents the magnitude of the output signal of the bridge circuit 16 obtained by conversion based on the stress distribution of the resistors R1 to R4 when changing the positions in which the resistors R1 to R4 are formed with respect to the center of the semiconductor chip 1X when a nut 52 of a clamp 50 is fixed at position P1 in the straight line 25 illustrated in FIG. 7 and reference numeral P2 represents the magnitude of the output signal of the bridge circuit 16 obtained by conversion based on the stress distribution of the resistors R1 to R4 when changing the positions in which the resistors R1 to R4 are formed with respect to the center of the semiconductor chip 1X when the nut 52 of the clamp 50 is fixed at position P2 in the straight line 26 illustrated in FIG. 7.

In the pressure sensor 901 having the rectangular semiconductor chip 1X, since the stress distribution on the semiconductor chip 1X greatly changes depending on the tightening position of the nut 52, the deviation of the resistance ratio of the four resistors disposed line-symmetrically with respect to a straight line 26 also changes depending on the tightening position of the nut 52. As a result, the shift amount of the zero point of a sensor output (an output signal of the bridge circuit 16 included in the strain gauge) greatly varies depending on the tightening position of the nut 52, as illustrated in FIGS. 7 and 8, in the pressure sensor 901.

In contrast, in the pressure sensor 100 according to embodiment 1, variations of the shift amount of the zero point of a sensor output (an output signal of the bridge circuit 16 included in the strain gauge) become smaller than in the pressure sensor 901 as described later. The pressure sensor 100 according to embodiment 1 will be described in detail below.

Figure 9:
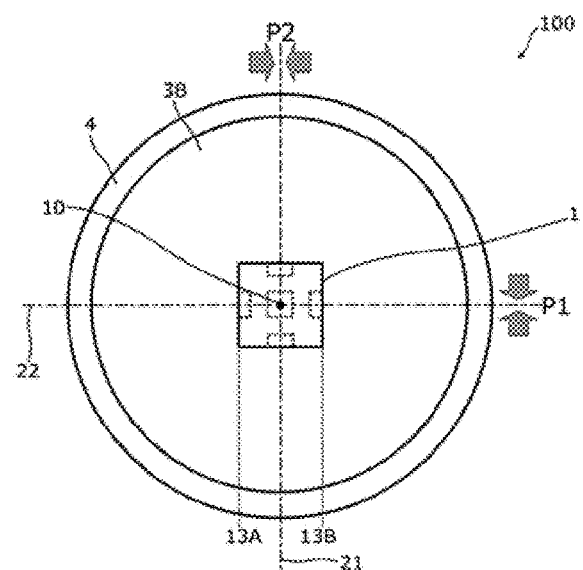
FIG. 9 illustrates the fixation position of a nut of a clamp for connecting a pipe to the pressure sensor according to embodiment 1.

FIG. 9 illustrates fixation positions of the nut of the clamp for connecting a pipe to the pressure sensor 100 according to embodiment 1.

Figure 10A:
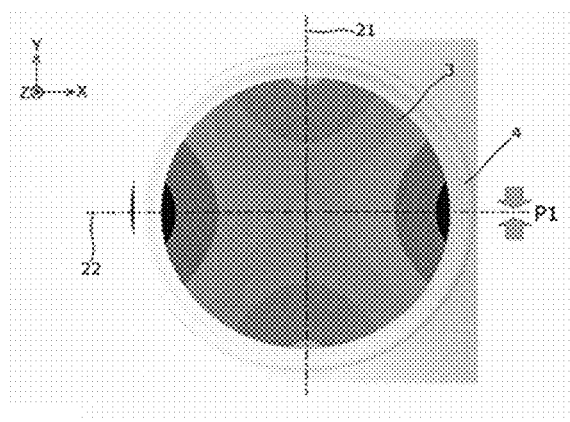
FIG. 10A is a contour diagram illustrating the displacement in the Z axis direction of the diaphragm 3 when a nut 52 of a clamp 50 is fixed at position P1 illustrated in FIG. 9.
Figure 10B:
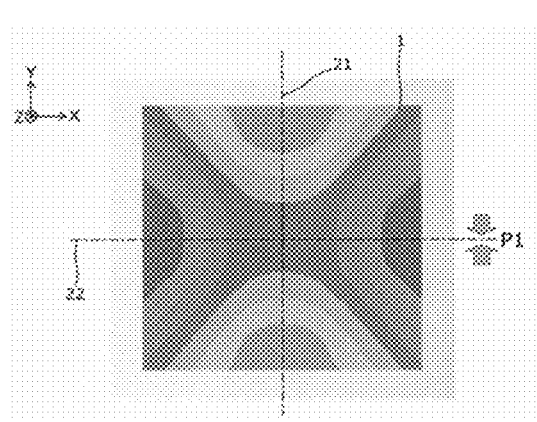
FIG. 10B is a contour diagram illustrating the displacement in the Z axis direction of a semiconductor chip 1 when the nut 52 of the clamp 50 is fixed at position P1 illustrated in FIG. 9.

FIG. 10A is a contour diagram (isoline diagram) illustrating the displacement in the Z axis direction of the diaphragm 3 when the nut 52 of the clamp 50 is fixed at position P1 in the straight line 22 illustrated in FIG. 9 and FIG. 10B is a contour diagram illustrating the displacement in the Z axis direction of the semiconductor chip 1 when the nut 52 of the clamp 50 is fixed at position P1 in the straight line 22 illustrated in FIG. 9.

FIG. 11A is a contour diagram (isoline diagram) illustrating the displacement in the Z axis direction of the diaphragm 3 when the nut 52 of the clamp 50 is fixed at position P2 in the straight line 21 illustrated in FIG. 9 and FIG. 11B is a contour diagram illustrating the displacement in the Z axis direction of the semiconductor chip 1 when the nut 52 of the clamp 50 is fixed at position P2 in the straight line 21 illustrated in FIG. 9.

In the contour diagrams in FIGS. 10A, 10B, 11A, and 11B, regions having the same displacement in the Z axis direction are given the same color.

FIG. 12 illustrates the result of simulation of an output signal of the bridge circuit 16 of the pressure sensor 100 using the FEM when the position of the nut 52 for fixing the clamp 50 is changed as illustrated in FIG. 9.

In FIG. 12, the horizontal axis represents the distance from the center 10 of the semiconductor chip 1 and the vertical axis represents the magnitude of the output signal (|Va−Vb|) of the bridge circuit 16 obtained by conversion based on the stress distribution of the four resistors R1 to R4 of the semiconductor chip 1.

In FIG. 12, reference numeral P1 represents the magnitude of the output signal of the bridge circuit 16 obtained by conversion based on the stress distribution of the resistors R1 to R4 when changing the positions in which the resistors R1 to R4 are formed with respect to the center of the semiconductor chip 1 when the nut 52 of the clamp 50 is fixed at position P1 in the straight line 22 illustrated in FIG. 9 and reference numeral P2 represents the magnitude of the output signal of the bridge circuit 16 obtained by conversion based on the stress distribution of the resistors R1 to R4 when changing the positions in which the resistors R1 to R4 are formed with respect to the center of the semiconductor chip 1 when the nut 52 of the clamp 50 is fixed at position P2 in the straight line 21 illustrated in FIG. 9.

As is clear from FIGS. 10A and 11A, when the position at which the nut 52 is tightened differs by 90 degrees in plan view in the pressure sensor 100 according to embodiment 1, the displacement in the Z axis direction of the diaphragm 3 is reversed. That is, the displacement in the Z direction of the diaphragm 3 when the nut 52 is fixed at position P1 differs in direction by 180 degrees from the displacement in the Z axis direction of the diaphragm 3 when the nut 52 is fixed at position P2.

At this time, since the supporting member 2a is fixed at the center 30 of the supporting surface 3B of the diaphragm 3 in plan view and the four supporting members 2b to 2e are fixed in the two straight lines 21 and 22, orthogonal to each other, that pass through the center 30 and the supporting members 2a to 2e support the semiconductor chip 1 that is square in plan view using the supporting surface 3B of the diaphragm 3 in the pressure sensor 100 according to embodiment 1, the displacement in the Z axis direction of the semiconductor chip 1 is also reversed as illustrated in FIGS. 10B and 11B.

In the pressure sensor 100 according to embodiment 1, the resistors R1 to R4 included in the strain gauge are disposed in the regions of the semiconductor chip 1 in which stress distributions in directions opposite to each other are generated when the clamp 50 is tightened by the nut 52. Specifically, as illustrated in FIG. 6, a pair of resistors (resistors R1 and R2) is formed in the region between the supporting member 2a and the supporting member 2b and another pair of resistors (resistors R3 and R4) is formed in the region between the supporting member 2a and the supporting member 2c.

Accordingly, when the nut 52 of the clamp 50 is tightened, stresses in directions opposite to each other are generated in the region between the supporting member 2a and the supporting member 2b in which the resistors R1 and R2 are formed and the region between the supporting member 2a and the supporting member 2c in which the resistors R3 and R4 are formed, so it is possible to align the directions in which the resistance values of the resistors R1 to R4 are changed due to the stresses by appropriately setting the directions in which the resistors R1 to R4 extend.

Specifically, the directions in which the resistors R1 to R4 extend only need to be determined so that the resistance value of the resistor R1 and the resistance value of the resistor R4 change in the same direction and the resistance value of the resistor R2 and the resistance value of the resistor R3 change in the same direction when the nut 52 of the clamp 50 is tightened. For example, as illustrated in FIG. 6, the resistor R1 and the resistor R4 extend in the same direction and the resistor R2 and the resistor R3 extend in the same direction. This changes the resistance values of the resistor R1 and the resistor R4 by substantially the same amount in the same direction and changes the resistance values of the resistor R2 and the resistor R3 by substantially the same amount in the same direction when the nut 52 of the clamp 50 is tightened.

As described above, by selecting the directions in which the resistor R1 and the resistor R4 extend so that the resistance values of the resistor R1 and the resistor R4 are changed in the same direction when the nut 52 of the clamp 50 is tightened, the deviation of the resistance ratio between the resistor R1 and the resistor R4 close to an output signal Va of the bridge circuit 16 included in the strain gauge can be suppressed. Similarly, by selecting the directions in which the resistor R2 and the resistor R3 extend so that the resistance values of the resistor R2 and the resistor R3 are changed in the same direction when the nut 52 of the clamp 50 is tightened, the deviation of the resistance ratio between the resistor R2 and the resistor R3 close to an output signal Vb of the bridge circuit 16 included in the strain gauge can be suppressed.

This can suppress fluctuations in the output signals Va and Vb of the bridge circuit 16 before and after the nut 52 of the clamp 50 is tightened and can also suppress variations in the fluctuation amount of the output signals Va and Vb when the position at which the nut 52 of the clamp 50 is tightened is changed. As a result, as illustrated in FIG. 12, the shift amount of the zero point of a sensor output (an output signal |Va−Vb| of the bridge circuit 16) of the pressure sensor 100 when the nut 52 of the clamp 50 is tightened is suppressed and variations in the above shift amount caused by the differences in the tightening position of the nut 52 of the clamp 50 can also be suppressed.

As described above, in the pressure sensor 100 according to embodiment 1, since fluctuations in the resistance ratio between the resistor R1 and the resistor R4 and fluctuations in the resistance ratio between the resistor R2 and the resistor R3 when the nut 52 of the clamp 50 is tightened can be suppressed by forming the resistors R1 and R2 and the resistors R3 and R4 in the region on the semiconductor chip 1 in which the displacement in the Z axis direction is reversed when the nut 52 of the clamp 50 is tightened, the shift amount of the zero point of a sensor output (output signal |Va−Vb| of the bridge circuit 16) of the pressure sensor 100 when the nut 52 of the clamp 50 is tightened can be suppressed and variations in the above shift amount caused by the differences in the tightening position of the nut 52 of the clamp 50 can also be suppressed.

In particular, when the resistor R1 and the resistor R4 extend in the same direction and the resistor R2 and the resistor R3 extend in the same direction, the resistance values of the resistor R1 and the resistor R4 can be changed by substantially the same amount in the same direction and the resistance values of the resistor R2 and the resistor R3 can be changed by substantially the same amount in the same direction when the nut 52 of the clamp 50 is tightened. Accordingly, the shift amount of the zero point of a sensor output (output signal |Va−Vb| of the bridge circuit 16) of the pressure sensor 100 when the nut 52 of the clamp 50 is tightened can be further suppressed and variations in the shift amount caused by the differences in the tightening position of the nut 52 of the clamp 50 can be further suppressed.

In addition, if the resistors R1 to R4 are formed in positions (for example, in the circumference of the circle 15) equidistant from the center 30 of the diaphragm 3 in plan view, it is possible to equalize the change amounts of the resistance values of the resistors R1 to R4 caused by stresses in the semiconductor chip 1 generated when the nut 52 is tightened, enabling further reduction in the shift amount of the zero point of a sensor output and variations in the shift amount.

In addition, since the deviation amount of the resistance ratio between the resistor R1 and the resistor R4 close to the output signal Va of the bridge circuit 16 and the deviation amount of the resistance ratio between the resistor R2 and the resistor R3 close to the output signal Vb of the bridge circuit 16 can be further increased when a pressure is applied to the pressure receiving surface 3A of the diaphragm 3 by the pressure from the measurement target fluid by making the direction in which the resistor R1 and the resistor R4 extend orthogonal to the direction in which the resistor R2 and the resistor R3 extend, the sensor sensitivity of the pressure sensor 100 with respect to the pressure applied to the pressure receiving surface 3A of the diaphragm 3 can be further improved.

In addition, since stresses easily concentrate on the resistors R1 to R4 by forming the resistors R1 to R4 in the regions corresponding to the thin-walled portion 1C of the semiconductor chip 1 in plan view, the sensor sensitivity of the pressure sensor 100 with respect to the pressure applied to the pressure receiving surface 3A of the diaphragm 3 can be further improved.

Although the pair of resistors R1 and R2 and the pair of resistors R3 and R4 are formed in the region between the supporting member 2a and the supporting member 2b and the region between the supporting member 2a and the supporting member 2c in plan view in the above embodiment (see FIG. 6), the resistors R1 to R4 only need to be disposed so that the resistance value of the resistor R1 and the resistance value of the resistor R4 are changed in the same direction and the resistance value of the resistor R2 and the resistance value of the resistor R3 are changed in the same direction when the nut 52 of the clamp 50 is tightened. For example, the resistors R1 to R4 may be disposed as illustrated in FIG. 13.

Figure 13:
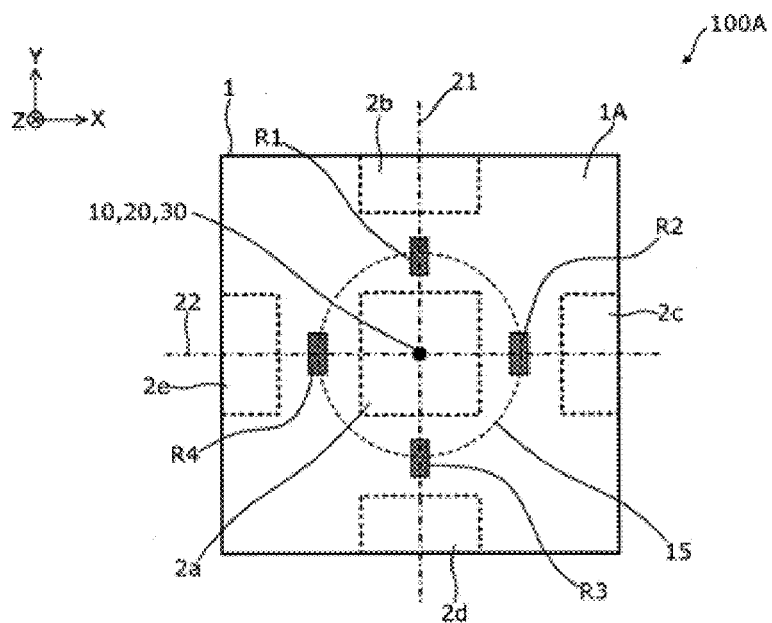
FIG. 13 illustrates another example of disposing the resistors in the pressure sensor according to embodiment 1.

FIG. 13 illustrates another example of disposing the resistors in the pressure sensor according to embodiment 1.

As illustrated in FIG. 13, each of the resistors R1 to R4 may be formed in the region between the coupling surface of the supporting member 2a and each of the coupling surfaces of the supporting members 2b to 2e in plan view in the semiconductor chip 1. Here, the resistors R1 to R4 are formed in, for example, rectangles in plan view and extend in the same direction.

Since this changes the resistance value of the resistor R1 and the resistance value of the resistor R4 in the same direction and changes the resistance value of the resistor R2 and the resistance value of the resistor R3 in the same direction when the nut 52 of the clamp 50 is tightened as in the example of disposing the resistors R1 to R4 illustrated in FIG. 6, the shift amount of the zero point of a sensor output and variations in the shift amount can be reduced.

Embodiment 2

Figure 14:
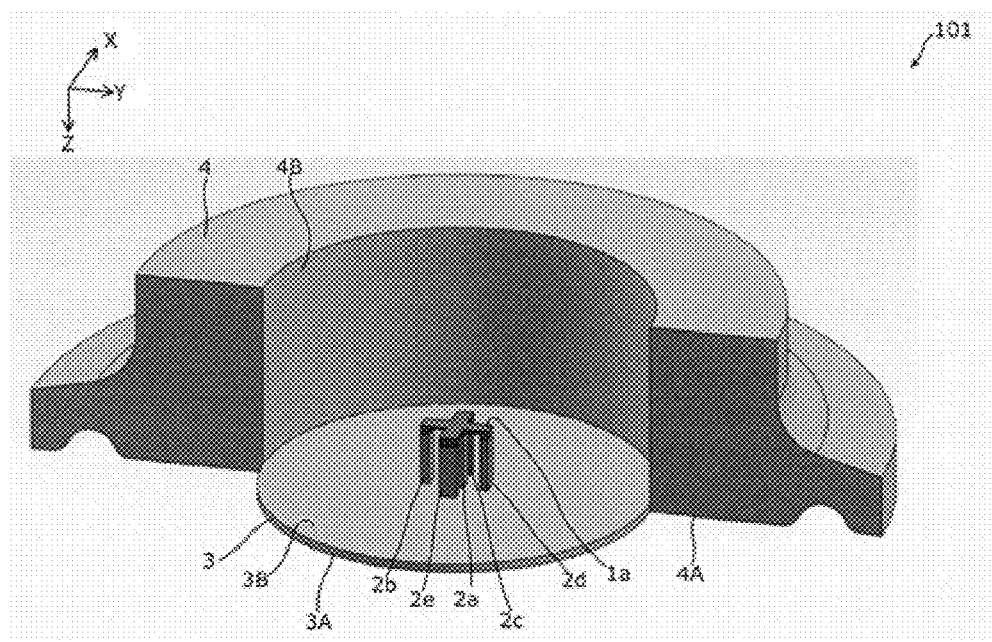
FIG. 14 is a perspective view illustrating the structure of a pressure sensor according to embodiment 2.
Figure 15:
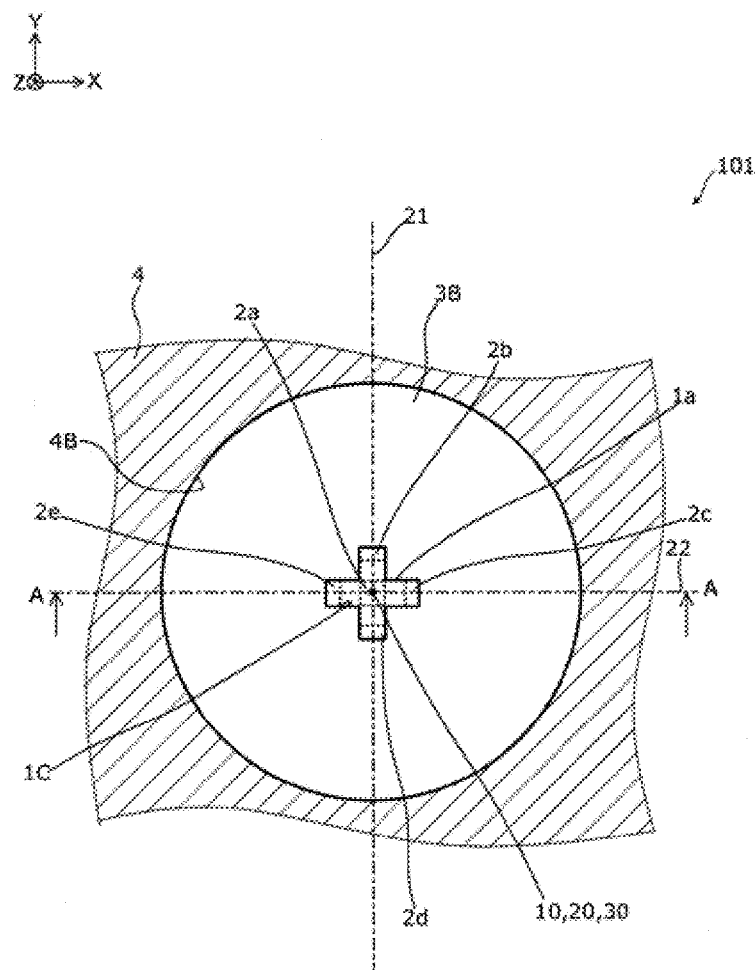
FIG. 15 is a plan view illustrating the structure of the pressure sensor according to embodiment 2.
Figure 16:
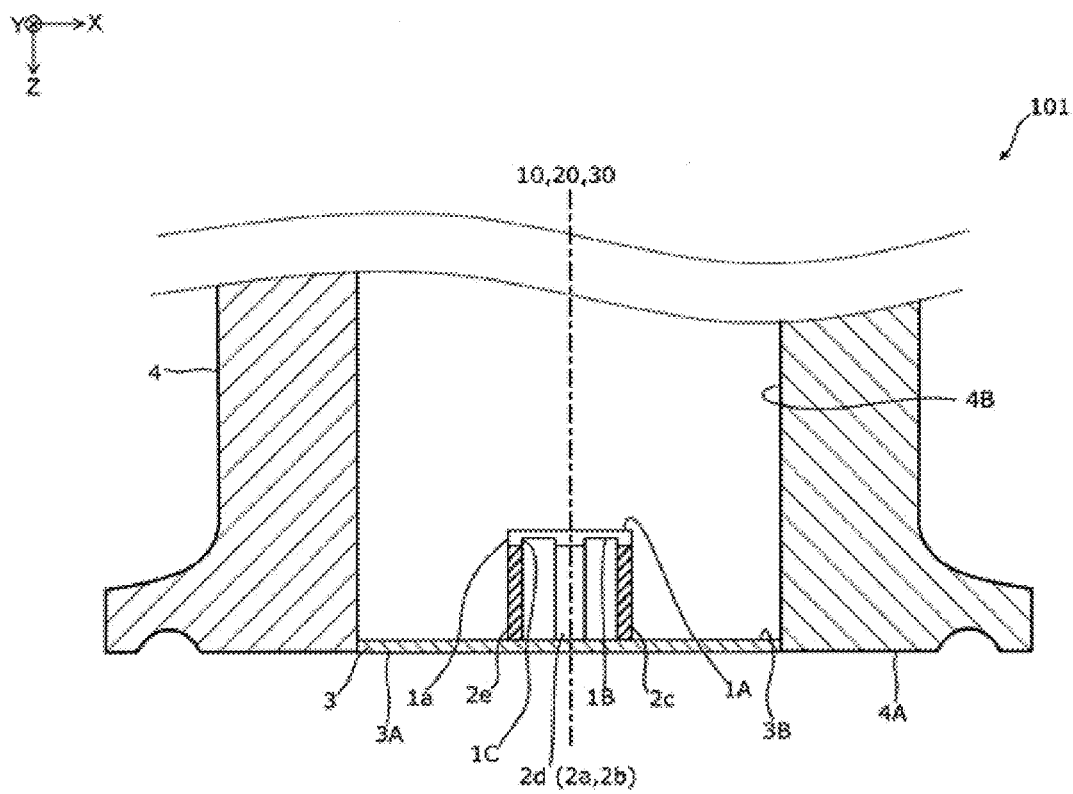
FIG. 16 is a cross-sectional view illustrating the structure of the pressure sensor according to embodiment 2.

FIGS. 14 to 16 illustrate the structure of a pressure sensor according to embodiment 2.

FIG. 14 is a perspective view illustrating a pressure sensor 101 according to embodiment 2, FIG. 15 illustrates the planar structure of the pressure sensor 101 seen from the Z direction in FIG. 14, and FIG. 16 illustrates the cross-sectional structure of the pressure sensor 101 taken along line A-A in FIG. 15. It should be noted that a cross-sectional structure along the axial line 21 is illustrated only for the cylindrical housing 4 in FIG. 14.

The pressure sensor 101 according to embodiment 2 is the same as the pressure sensor 100 according to embodiment 1 except that the semiconductor chip 1a has a shape (that is, a cross shape in plan view) obtained by cutting out four squares each including one corner of the square semiconductor chip.

As illustrated in FIGS. 14 to 16, the supporting member 2a as the first structural body is provided orthogonally so that one end thereof is coupled to the center 30 of the supporting surface 3B of the diaphragm 3 in plan view and the other end thereof is coupled to the center 10 of the back surface 1B of the semiconductor chip 1a in plan view.

In addition, as illustrated in FIGS. 14 to 16, the supporting members 2b to 2e as the second structural bodies have one ends coupled to the supporting surface 3B and the other ends coupled to four arms 11b to 11e of the back surface 1B of the cross semiconductor chip 1a.

Figure 17:
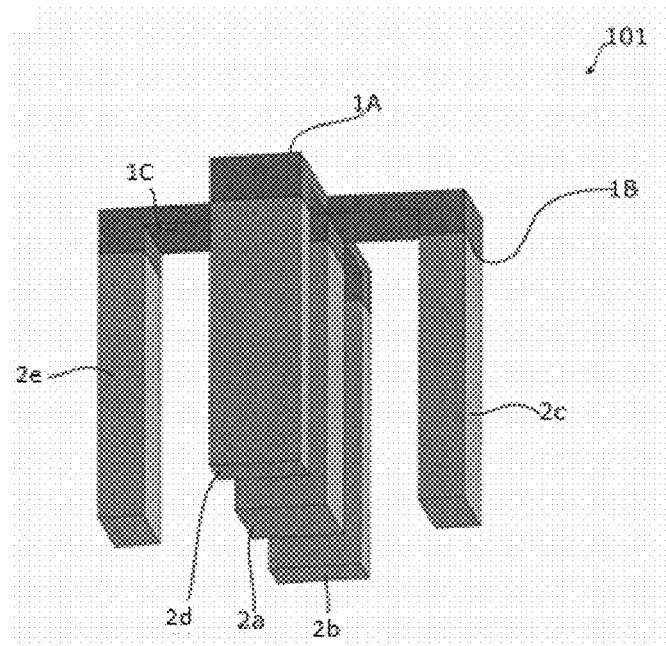
FIG. 17 is a perspective view illustrating a semiconductor chip of the pressure sensor according to embodiment 2 seen from a back surface.

FIG. 17 is a perspective view illustrating the semiconductor chip 1a of the pressure sensor 101 according to embodiment 2 seen from the back surface.

As illustrated in FIG. 17, the thin-walled portion 1C thinner than the part to which the supporting members 2a to 2e are coupled is formed on the back surface 1B of the semiconductor chip 1a as in the semiconductor chip 1 according to embodiment 1.

In the pressure sensor 101, when a pressure larger than the pressure (atmospheric pressure) applied to the supporting surface 3B is applied to the pressure receiving surface 3A of the diaphragm 3 and the diaphragm 3 is bent according to the pressure difference between the pressures applied to both surfaces of the diaphragm 3, the semiconductor chip 1a is distorted via the supporting members 2a to 2e and a stress is generated mainly in the thin-walled portion 1C. The resistors R1 to R4 constituting the strain gauge (bridge circuit) are formed in the region in which this tensile stress is generated.

Figure 18:
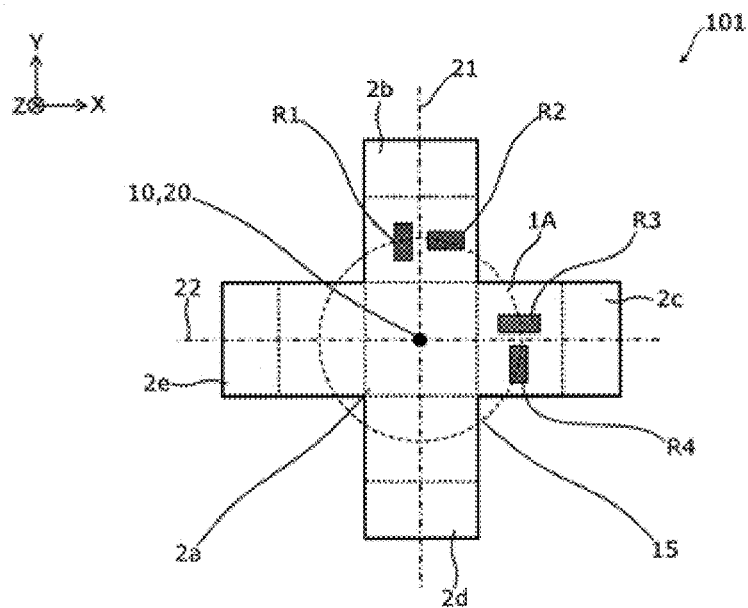
FIG. 18 illustrates an example of disposing resistors on the semiconductor chip in the pressure sensor according to embodiment 2.

FIG. 18 illustrates an example of disposing the resistors R1 to R4 on the semiconductor chip 1a in the pressure sensor 101 according to embodiment 2.

As illustrated in FIG. 18, the resistors R1 and R2 are formed in the region on the principal surface 1A corresponding to the thin-walled portion 1C between the coupling surface of the supporting member 2b and the coupling surface of the supporting member 2a disposed in the straight line 21 in plan view. In addition, the resistors R3 and R4 are formed in the region on the principal surface 1A corresponding to the thin-walled portion 1C between the coupling surface of the supporting member 2c and the coupling surface of the supporting member 2a disposed in the straight line 22 in plan view.

In addition, as illustrated in FIG. 18, the resistors R1 to R4 are disposed equidistantly (within a deviation of, for example, plus or minus 10 percent) from the center 20 of the supporting member 2a in plan view. In addition, the direction in which the resistor R1 and the resistor R4 extend is orthogonal to the direction in which the resistor R2 and the resistor R3 extend.

Figure 19:
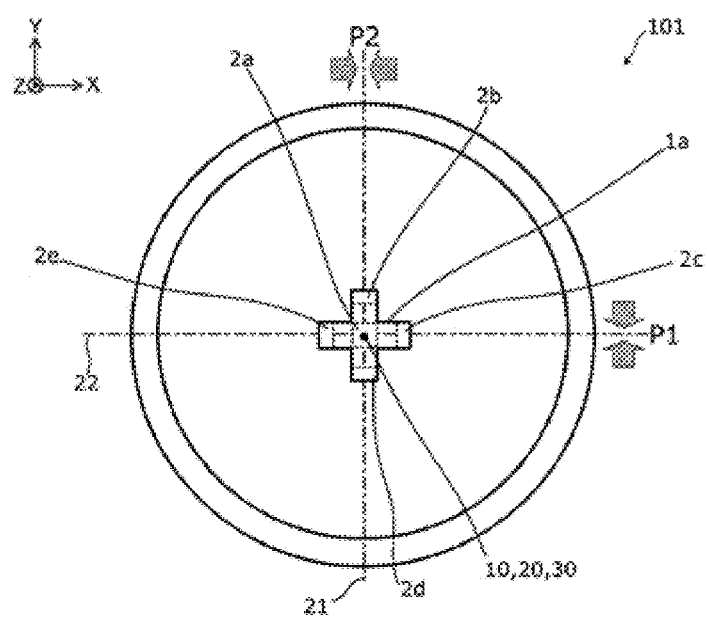
FIG. 19 illustrates the fixation position of a nut of a clamp for connecting a pipe to the pressure sensor according to embodiment 2.

FIG. 19 illustrates fixation positions of the nut of the clamp for connecting a pipe to the pressure sensor 101 according to embodiment 2.

Figure 20:
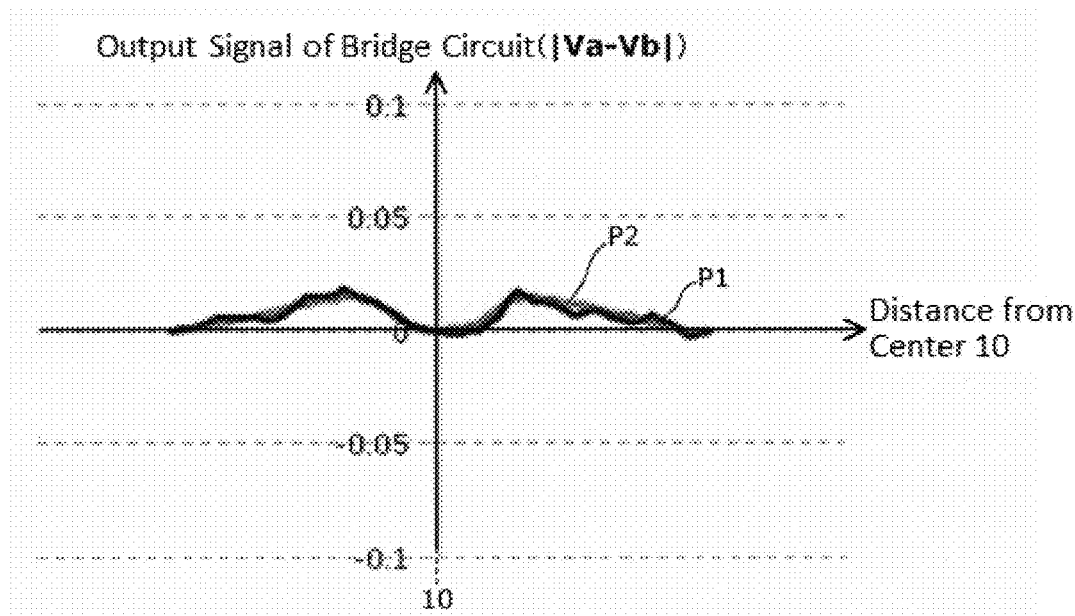
FIG. 20 illustrates the result of simulation of a sensor output from the pressure sensor according to embodiment 2.

FIG. 20 illustrates the result of simulation of an output signal of the bridge circuit 16 of the pressure sensor 101 using the FEM when the position of the nut 52 for fixing the clamp 50 is changed as illustrated in FIG. 19.

In FIG. 20, the horizontal axis represents the distance from the center 10 of the semiconductor chip 1a and the vertical axis represents the magnitude of the output signal (|Va−Vb|) of the bridge circuit 16 obtained by conversion based on the stress distribution of the four resistors R1 to R4 of the semiconductor chip 1a. In FIG. 20, reference numeral P1 represents the magnitude of the output signal of the bridge circuit 16 obtained by conversion based on the stress distribution of the resistors R1 to R4 when changing the positions in which the resistors R1 to R4 are formed with respect to the center of the semiconductor chip 1a when the nut 52 of the clamp 50 is fixed at position P1 in the straight line 22 illustrated in FIG. 19 and reference numeral P2 represents the magnitude of the output signal of the bridge circuit 16 obtained by conversion based on the stress distribution of the resistors R1 to R4 when changing the positions in which the resistors R1 to R4 are formed with respect to the center of the semiconductor chip 1a when the nut 52 of the clamp 50 is fixed at position P2 in the straight line 21 illustrated in FIG. 19.

In the pressure sensor 101 according to embodiment 2, the resistors R1 and R4 and the resistors R2 and R3 are formed in the region on the semiconductor chip 1a in which the displacement in the Z axis direction is reversed when the clamp 50 is tightened by the nut 52 as in the pressure sensor 100 according to embodiment 1, fluctuations in the resistance ratio between the resistor R1 and the resistor R4 and fluctuations in the resistance ratio between the resistor R2 and the resistor R3 when the nut 52 of the clamp 50 is tightened can be suppressed. As illustrated in FIG. 20, this can suppress the shift amount of the zero point of a sensor output (output signal |Va−Vb| of the bridge circuit 16) of the pressure sensor 101 when the nut 52 of the clamp 50 is tightened and also suppress variations in the above shift amount caused by the differences in the tightening position of the nut 52 of the clamp 50.

In particular, if the resistor R1 and the resistor R4 extend in the same direction and the resistor R2 and the resistor R3 extend in the same direction, the shift amount of the zero point of a sensor output of the pressure sensor 101 when the nut 52 of the clamp 50 is tightened can be further suppressed and variations in the shift amount can be further suppressed as in the pressure sensor 100 according to embodiment 1.

In addition, if the resistors R1 to R4 are formed equidistantly (for example, in the circumference of the circle 15) from the center 30 of the diaphragm 3 in plan view, the shift amount of the zero point of a sensor output of the pressure sensor 101 when the nut 52 of the clamp 50 is tightened can be further suppressed and variations in the shift amount can be further suppressed as in the pressure sensor 100 according to embodiment 1.

In addition, by making the direction in which the resistor R1 and the resistor R4 extend orthogonal to the direction in which the resistor R2 and the resistor R3 extend, the sensor sensitivity of the pressure sensor 101 with respect to the pressure applied to the pressure receiving surface 3A of the diaphragm 3 can be further improved as in the pressure sensor 100 according to embodiment 1.

In addition, the sensor sensitivity of the pressure sensor 101 with respect to the pressure applied to the pressure receiving surface 3A of the diaphragm 3 can be further improved by forming the resistors R1 to R4 in the regions corresponding to the thin-walled portion 1C of the semiconductor chip 1a in plan view.

In addition, since the semiconductor chip 1a is formed in a cross in the pressure sensor 101 according to embodiment 2, stresses are easily concentrated on the region in which the resistors R1 to R4 are formed as compared with the rectangular semiconductor chip and the sensor sensitivity of the pressure sensor 101 with respect to the pressure applied to the pressure receiving surface 3A of the diaphragm 3 can be further improved.

Although the pair of resistors R1 and R2 and the pair of resistors R3 and R4 are formed in the region between the supporting member 2a and the supporting member 2b and the region between the supporting member 2a and the supporting member 2c in plan view in embodiment 2 (see FIG. 18), the resistors R1 to R4 only need to be disposed so that the resistance value of the resistor R1 and the resistance value of the resistor R4 are changed in the same direction and the resistance value of the resistor R2 and the resistance value of the resistor R3 are changed in the same direction when the nut 52 of the clamp 50 is tightened. For example, the resistors R1 to R4 may be disposed as illustrated in FIG. 21.

Figure 21:
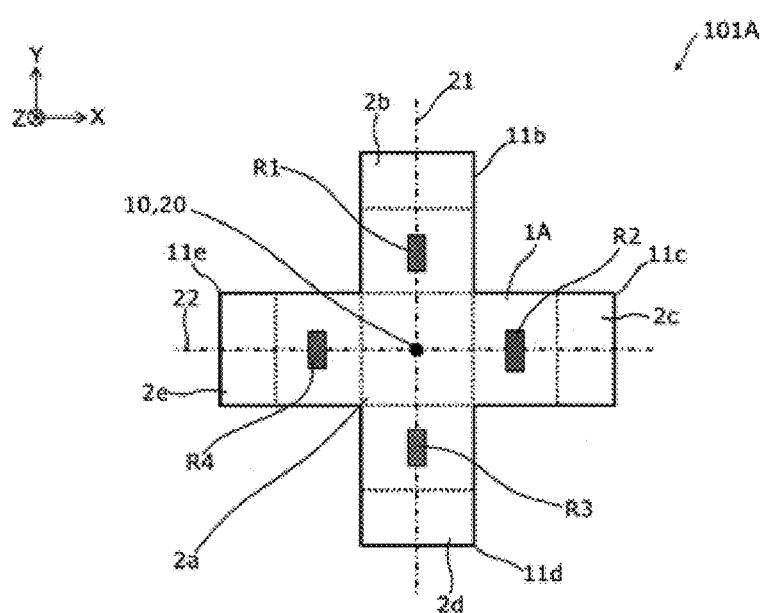
FIG. 21 illustrates an example of disposing resistors on the semiconductor chip in another pressure sensor according to embodiment 2.

FIG. 21 illustrates an example of disposing resistors on a semiconductor chip in the other pressure sensor according to embodiment 2.

As illustrated in FIG. 21, in a pressure sensor 101A, each of the resistors R1 to R4 may be formed in the region between the coupling surface of the supporting member 2a and each of the coupling surfaces of the supporting members 2b to 2e in plan view in the semiconductor chip 1a. Here, the resistors R1 to R4 are formed in, for example, rectangles in plan view and extend in the same direction.

Since this changes the resistance value of the resistor R1 and the resistance value of the resistor R4 in the same direction and changes the resistance value of the resistor R2 and the resistance value of the resistor R3 in the same direction when the nut 52 of the clamp 50 is tightened as in the example of disposing the resistors R1 to R4 illustrated in FIG. 18, the shift amount of the zero point of a sensor output and variations in the shift amount can be reduced.

Embodiment 3

Figure 22:
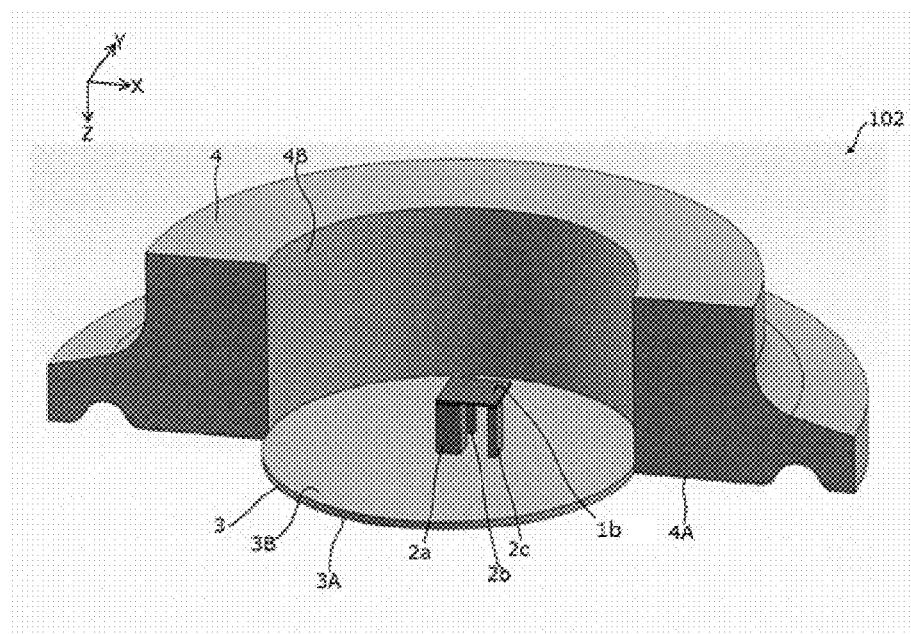
FIG. 22 is a perspective view illustrating the structure of a pressure sensor according to embodiment 3.
Figure 23:
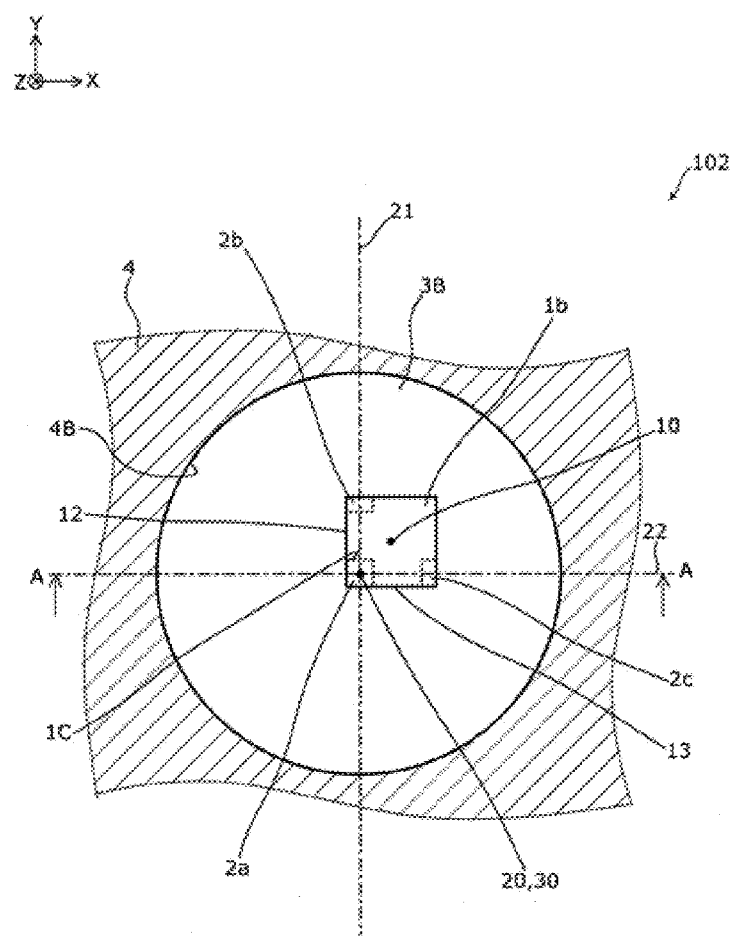
FIG. 23 is a plan view illustrating the structure of the pressure sensor according to embodiment 3.
Figure 24:
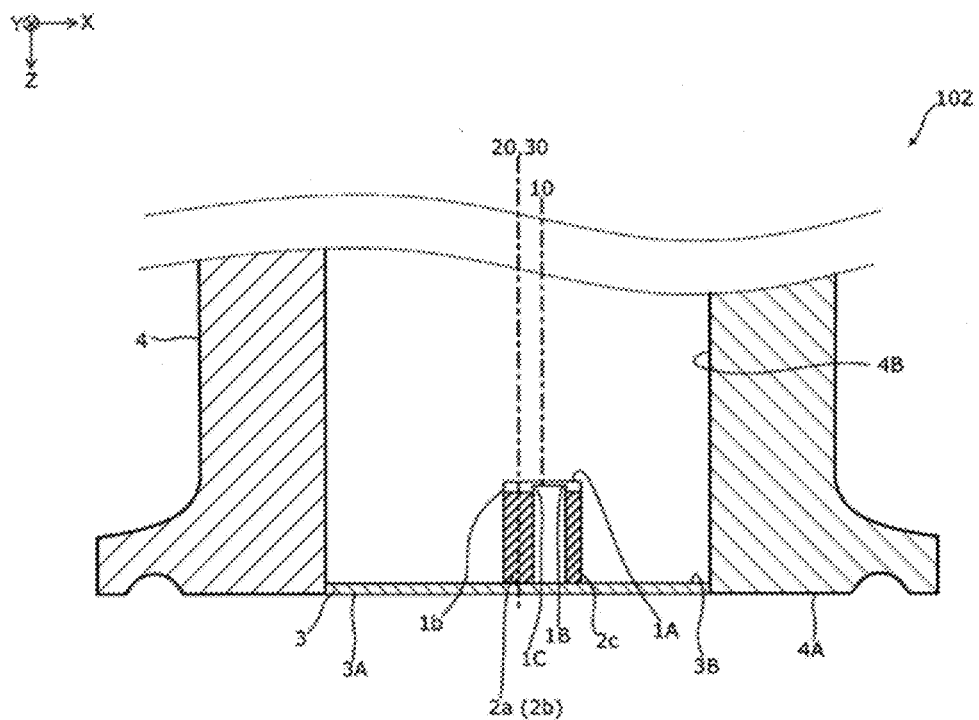
FIG. 24 is a cross-sectional view illustrating the structure of the pressure sensor according to embodiment 3.

FIGS. 22 to 24 illustrate the structure of a pressure sensor according to embodiment 3.

FIG. 22 is a perspective view illustrating a pressure sensor 102 according to embodiment 3, FIG. 23 illustrates the planar structure of the pressure sensor 102 seen from the Z direction in FIG. 22, and FIG. 24 illustrates the cross-sectional structure of the pressure sensor 102 taken along line A-A in FIG. 23. It should be noted that a cross-sectional structure along the axial line 22 is illustrated only for the housing 4 in FIG. 22.

The pressure sensor 102 according to embodiment 3 is the same as the pressure sensor 100 according to embodiment 1 except that a semiconductor chip 1b is supported by three columns (supporting members) provided orthogonally to the supporting surface 3B of the diaphragm 3 and the center 10 of the semiconductor chip 1b does not coincide with the center 30 of the diaphragm in plan view.

As illustrated in FIGS. 22 to 24, the semiconductor chip 1b is formed in a square in plan view.

As illustrated in FIGS. 22 to 24, the supporting member 2a as the first structural body has one end coupled to the center 30 of the supporting surface 3B of the diaphragm 3 in plan view and the other end coupled to a region including one corner of the back surface 1B of the semiconductor chip 1b in plan view.

In addition, as illustrated in FIGS. 22 to 24, the supporting members 2b and 2c as the second structural bodies are provided in the two straight lines 21 and 22 separately from the supporting member 2a in plan view so that one ends thereof are coupled to the supporting surface 3B and the other ends thereof are coupled to the back surface 1B of the semiconductor chip 1b.

Specifically, the one end of the supporting member 2b is coupled in the straight line 21 on the supporting surface 3B in plan view and the one end of the supporting member 2c is disposed in the straight line 22 on the supporting surface 3B in plan view. In addition, the other end of the supporting member 2b is disposed along one side 12 of the corner of the semiconductor chip 1b to which the supporting member 2a of the semiconductor chip 1b is coupled and the other end of the supporting member 2c is disposed along the other side 13 of the corner of the semiconductor chip 1b to which the supporting member 2a of the semiconductor chip 1b is coupled.

Figure 25:
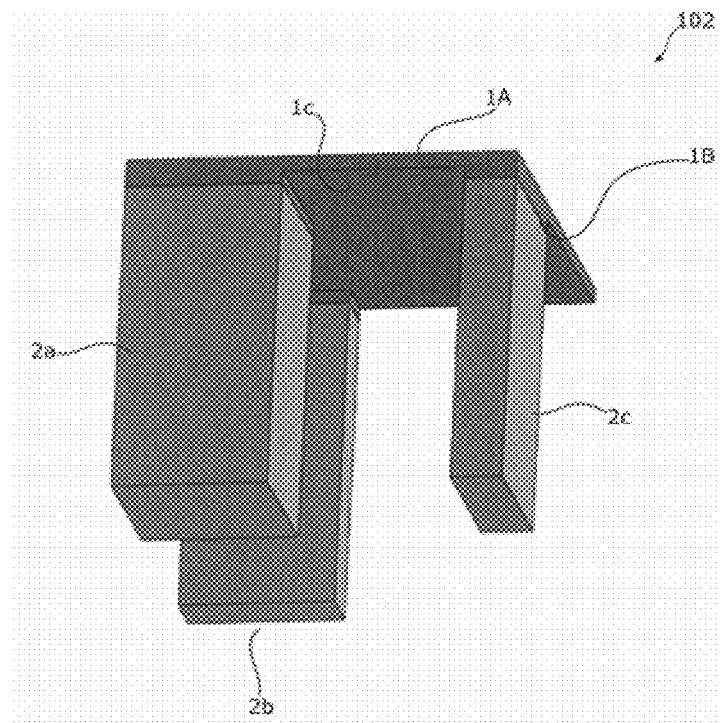
FIG. 25 is a perspective view illustrating a semiconductor chip of the pressure sensor according to embodiment 3 seen from a back surface.

FIG. 25 is a perspective view illustrating the semiconductor chip 1b of the pressure sensor 102 according to embodiment 3 seen from the back surface.

As illustrated in FIG. 25, the thin-walled portion 1C thinner than the part to which the supporting members 2a to 2c are coupled is formed on the back surface 1B of the semiconductor chip 1b as in the semiconductor chip 1 according to embodiment 1.

In the pressure sensor 102, when a pressure larger than the pressure (atmospheric pressure) applied to the supporting surface 3B is applied to the pressure receiving surface 3A of the diaphragm 3 and the diaphragm 3 is bent according to the pressure difference between the pressures applied to both surfaces of the diaphragm 3, the semiconductor chip 1b is distorted via the supporting members 2a to 2c and a stress is generated mainly in the thin-walled portion 1C. The resistors R1 to R4 constituting the strain gauge (bridge circuit) are formed in the region in which this tensile stress is generated.

Preferably, the supporting member 2a is not inclined toward the X axis direction or the Y axis direction when a pressure larger than in the supporting surface 3B is applied to the pressure receiving surface 3A of the diaphragm 3. Therefore, in the pressure sensor 102 according to embodiment 3, the rigidness of the supporting member 2a is improved by making the supporting member 2a thicker than the other supporting members 2b and 2c. For example, when the supporting members 2a to 2c are columnar members (such as cylindrical or rectangular columns) having the same length in the Z axis direction as illustrated in FIGS. 21 to 24, the area of the cross section parallel to the X-Y plane of the supporting member 2a is larger than the areas of the cross sections parallel to the X-Y plane of the supporting members 2b and 2c.

Figure 26:
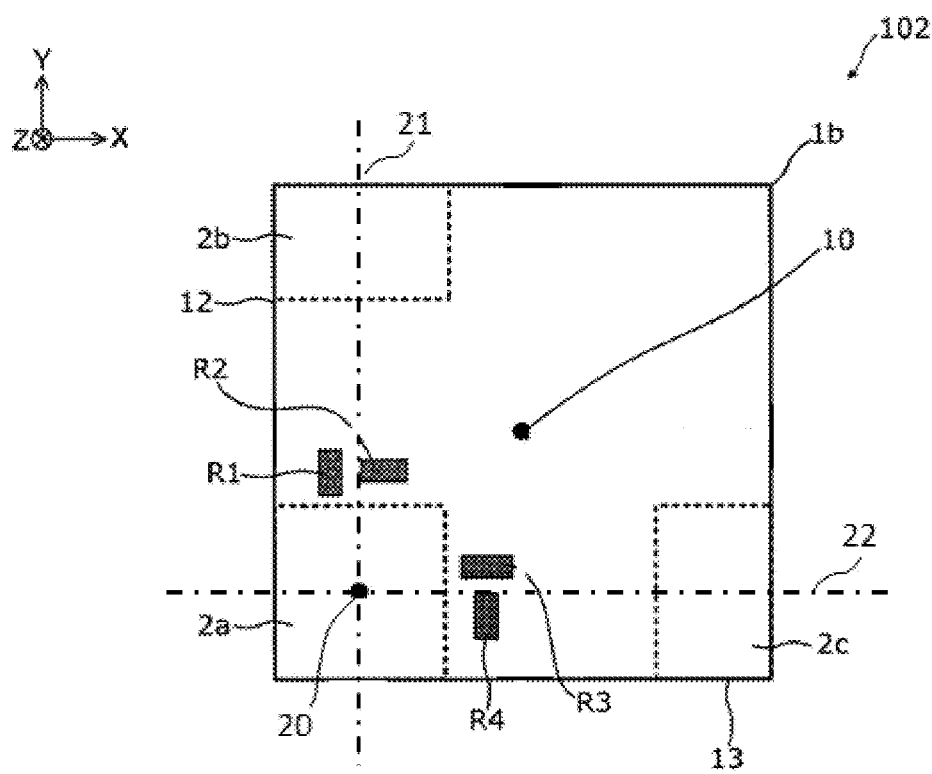
FIG. 26 illustrates an example of disposing resistors on the semiconductor chip in the pressure sensor according to embodiment 3.

FIG. 26 illustrates an example of disposing the resistors R1 to R4 on the semiconductor chip 1b in the pressure sensor 102 according to embodiment 3.

As illustrated in FIG. 26, the resistors R1 and R2 are formed in the region on the principal surface 1A corresponding to the thin-walled portion 1C between the coupling surface of the supporting member 2b and the coupling surface of the supporting member 2a, the region being disposed in the straight line 21 in plan view. In addition, the resistors R3 and R4 are formed in the region on the principal surface 1A corresponding to the thin-walled portion 1C between the coupling surface of the supporting member 2c and the coupling surface of the supporting member 2a, the region being disposed in the straight line 22 in plan view.

In addition, the direction in which the resistor R1 and the resistor R4 extend is orthogonal to the direction in which the resistor R2 and the resistor R3 extend.

In addition, the resistors R1 to R4 are disposed equidistantly (within a deviation of, for example, plus or minus 10 percent) from the center 20 of the supporting member 2a in plan view.

In the pressure sensor 102 according to embodiment 3, the resistors R1 and R4 and the resistors R2 and R3 are formed in the region on the semiconductor chip 1b in which the displacement in the Z axis direction is reversed when the clamp 50 is tightened by the nut 52 as in the pressure sensor 100 according to embodiment 1, fluctuations in the resistance ratio between the resistor R1 and the resistor R4 and fluctuations in the resistance ratio between the resistor R2 and the resistor R3 when the nut 52 of the clamp 50 is tightened can be suppressed.

As in the pressure sensor 100 according to embodiment 1, this can suppress the shift amount of the zero point of a sensor output (output signal |Va−Vb| of the bridge circuit 16) of the pressure sensor 102 when the nut 52 of the clamp 50 is tightened and also suppress variations in the above shift amount caused by the differences in the tightening position of the nut 52 of the clamp 50.

In particular, as in the pressure sensor 100 according to embodiment 1, if the resistor R1 and the resistor R4 extend in the same direction and the resistor R2 and the resistor R3 extend in the same direction, the shift amount of the zero point of a sensor output of the pressure sensor 102 when the nut 52 of the clamp 50 is tightened can be further suppressed and variations in the shift amount can be further suppressed.

In addition, as in the pressure sensor 100 according to embodiment 1, if the resistors R1 to R4 are formed equidistantly (for example, in the circumference of the circle 15) from the center 30 of the diaphragm 3 in plan view, the shift amount of the zero point of a sensor output of the pressure sensor 102 when the nut 52 of the clamp 50 is tightened can be further suppressed and variations in the above shift amount can be further suppressed.

Figure 27:
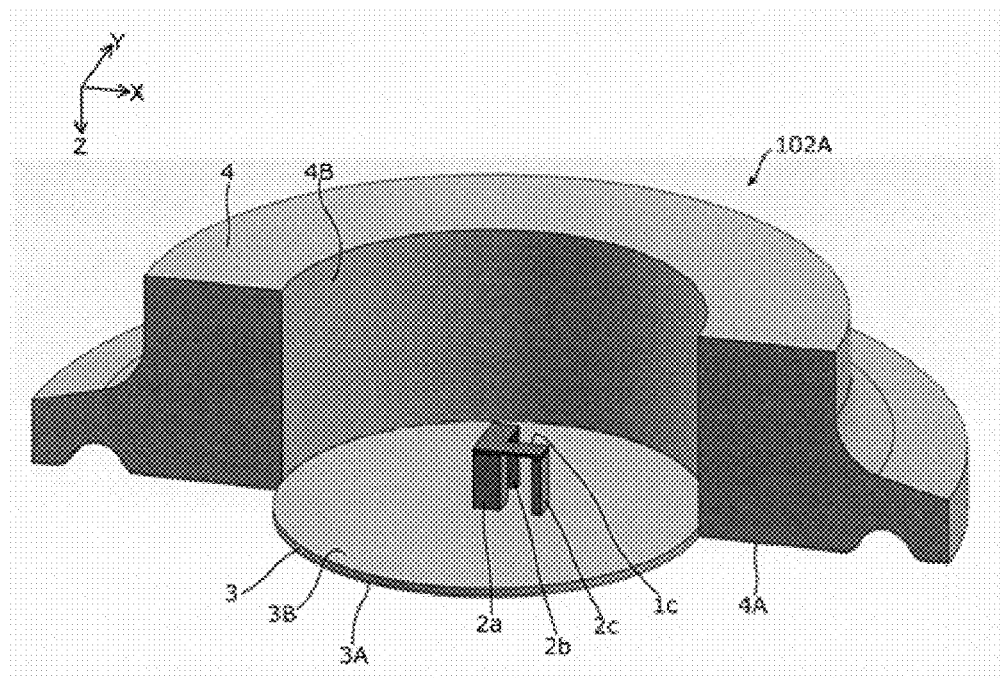
FIG. 27 is a perspective view illustrating the structure of another pressure sensor according to embodiment 3.
Figure 28:
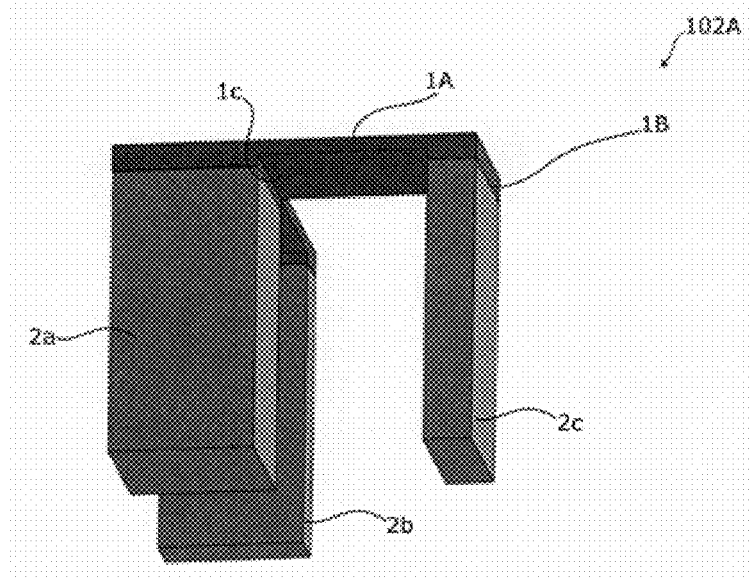
FIG. 28 is a perspective view illustrating a semiconductor chip of the other pressure sensor according to embodiment 3 seen from a back surface.

Although the semiconductor chip is square in plan view in embodiment 3 (see FIG. 26), the invention is not limited to this embodiment and the semiconductor chip may be L-shaped as illustrated in FIGS. 27 and 28.

FIGS. 27 and 28 illustrate the structure of the other pressure sensor according to embodiment 3.

FIG. 27 is a perspective view illustrating another pressure sensor 102A according to embodiment 3 and FIG. 28 is a perspective view illustrating the other pressure sensor 102A seen from the back surface 1B of a semiconductor chip 1c.

As illustrated in FIGS. 27 and 28, the semiconductor chip 1c may have a shape in which the inner angle of the corner to which the supporting member 2a, 2b, or 2c is not coupled is larger than 180 degrees. In other words, the semiconductor chip 1c may have an L-shape obtained by cutting out a square including a corner from the rectangular semiconductor chip 1b.

Figure 29:
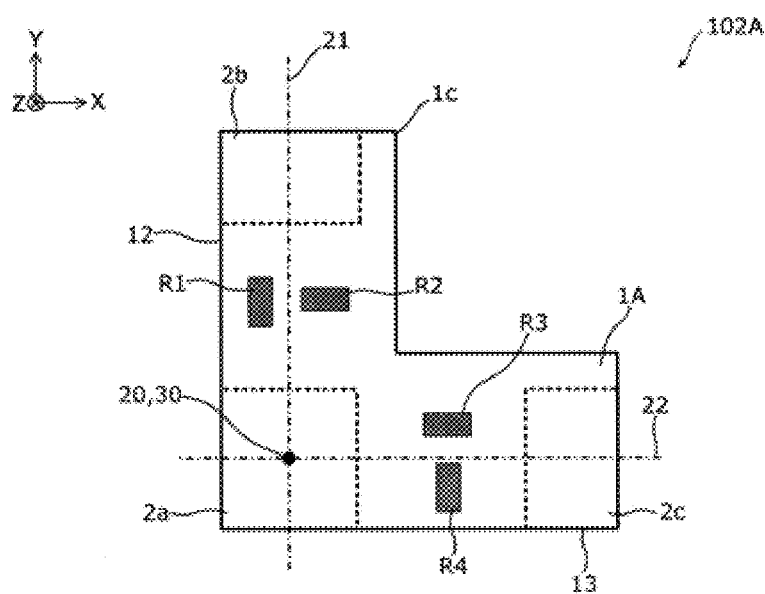
FIG. 29 illustrates an example of disposing resistors on the semiconductor chip in the other pressure sensor according to embodiment 3.

FIG. 29 illustrates an example of disposing the resistors R1 to R4 on the semiconductor chip 1c in the other pressure sensor 102A according to embodiment 3.

As illustrated in FIG. 29, the resistors R1 and R2 are formed in the region on the principal surface 1A corresponding to the thin-walled portion 1C between the coupling surface of the supporting member 2b and the coupling surface of the supporting member 2a disposed in the straight line 21 in plan view, as in the pressure sensor 102 according to embodiment 3. In addition, the resistors R3 and R4 are formed in the region on the principal surface 1A corresponding to the thin-walled portion 1C between the coupling surface of the supporting member 2c and the coupling surface of the supporting member 2a disposed in the straight line 22 in plan view, as in the pressure sensor 102 according to embodiment 3.

In addition, the supporting member 2a is formed so as to be thicker than the other supporting members 2b and 2c, as in the pressure sensor 102 according to embodiment 3.

As described above, in the other pressure sensor 102A according to embodiment 3, the shift amounts of the zero points of sensor outputs (output signals Va and Vb) when the nut 52 of the clamp 50 is tightened and variations in the shift amounts can be suppressed as in the pressure sensor 102 according to embodiment 3.

In addition, since the semiconductor chip 1c has a shape obtained by cutting out a square including one corner from the rectangular semiconductor chip 1 (or 1b) in the other pressure sensor 102A according to embodiment 3, as compared with a rectangular semiconductor chip, stresses are easily concentrated on the region in which the resistors R1 to R4 are formed and the sensor sensitivity of the pressure sensor 102A with respect to the pressure applied to the pressure receiving surface 3A of the diaphragm 3 can be further improved.

Embodiment 4

Figure 30:
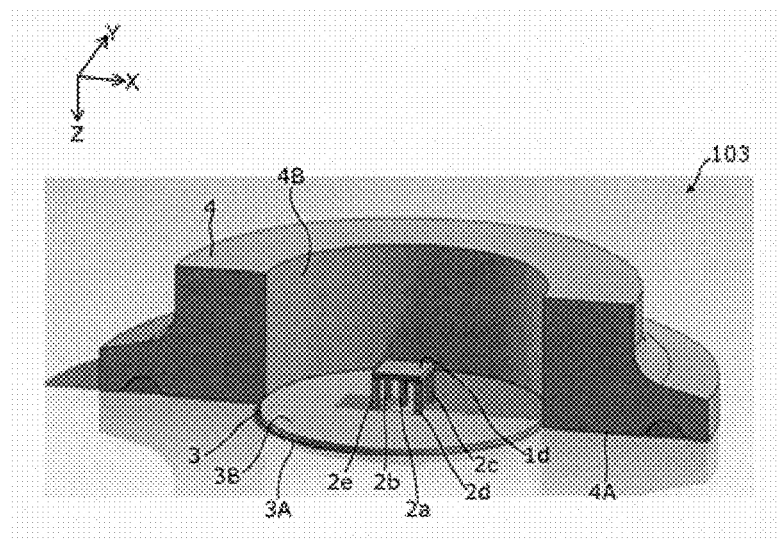
FIG. 30 is a perspective view illustrating the structure of a pressure sensor according to embodiment 4.
Figure 31:
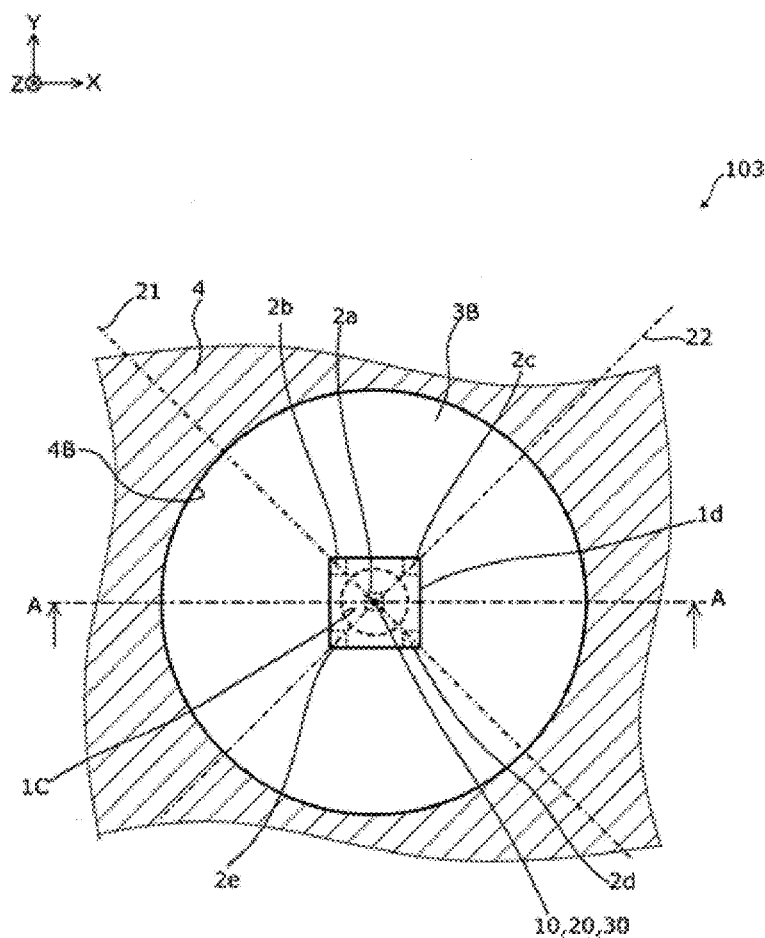
FIG. 31 is a plan view illustrating the structure of the pressure sensor according to embodiment 4.
Figure 32:
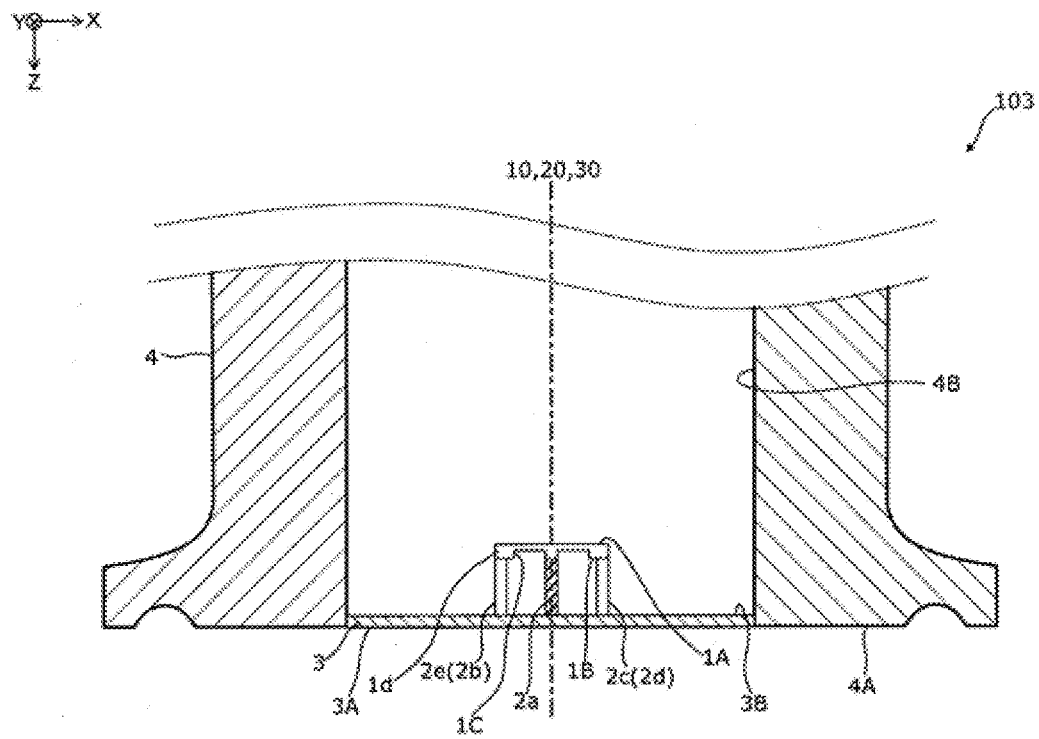
FIG. 32 is a cross-sectional view illustrating the structure of the pressure sensor according to embodiment 4.

FIGS. 30 to 32 illustrate the structure of a pressure sensor according to embodiment 4.

FIG. 30 is a perspective view illustrating a pressure sensor 103 according to embodiment 4, FIG. 31 illustrates the planar structure of the pressure sensor 103 seen from the Z direction in FIG. 30, and FIG. 32 illustrates the cross-sectional structure of the pressure sensor 103 taken along line A-A in FIG. 31. It should be noted that a cross-sectional structure along the axial line A-A is illustrated only for the housing 4 in FIG. 30.

The pressure sensor 103 according to embodiment 4 is the same as the pressure sensor 100 according to embodiment 1 except that the four supporting members 2b to 2e as the second structural bodies are coupled to four corners of a semiconductor chip 1d.

As illustrated in FIGS. 30 to 32, the semiconductor chip 1d is formed in a square in plan view.

The supporting member 2a as the first structural body is coupled to the supporting surface 3B so that the center 20 of the supporting member 2a coincides with the center 30 of the diaphragm and the center 10 of the semiconductor chip 1d in plan view, as in the pressure sensor 100 according to embodiment 1.

As illustrated in FIGS. 30 to 32, the supporting members 2b to 2e as the second structural bodies are provided orthogonally to the supporting surface 3B so that one ends thereof are coupled to the regions on the supporting surface 3B in which the diaphragm 3 is deformed when a pressure larger than in the supporting surface 3B is applied to the pressure receiving surface 3A and the other ends thereof are coupled to the four corners of the back surface 1B of the semiconductor chip 1d. More specifically, the supporting members 2b to 2e are disposed in the straight lines 21 and 22, which are the diagonal lines of the semiconductor chip 1d that pass through the center 20 of the supporting member 2a and the center 30 of the diaphragm in plan view, so as to be coupled to the four corners of the back surface 1B of the semiconductor chip 1d.

Figure 33:
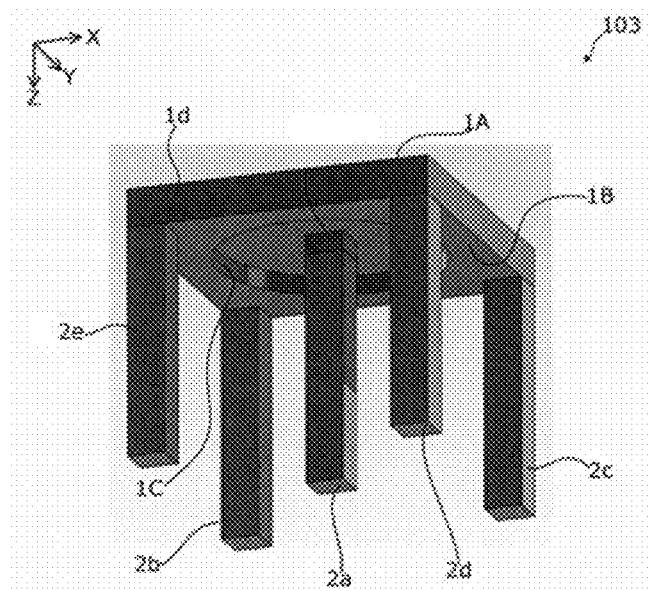
FIG. 33 is a perspective view illustrating a semiconductor chip of the pressure sensor according to embodiment 4 seen from a back surface.

FIG. 33 is a perspective view illustrating the semiconductor chip 1d of the pressure sensor 103 according to embodiment 4 seen from the back surface 1B.

As illustrated in FIG. 33, the thin-walled portion 1C that is circular in plan view and thinner than the part to which the supporting members 2a to 2e are coupled is formed on the back surface 1B of the semiconductor chip 1d as in the semiconductor chip 1 according to embodiment 1.

Figure 34:
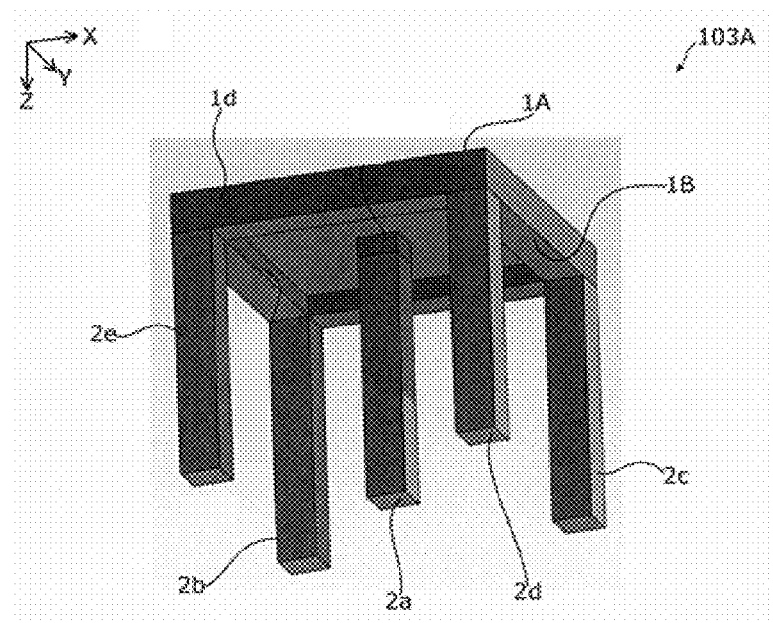
FIG. 34 is a perspective view illustrating another shape of a thin-walled portion of the semiconductor chip in the pressure sensor according to embodiment 4.

It should be noted that the shape of the thin-walled portion 1C in plan view is not specially limited. For example, the shape may be rectangular in plan view as in a pressure sensor 103A illustrated in FIG. 34.

In the pressure sensor 103, when a pressure larger than the pressure (atmospheric pressure) applied to the supporting surface 3B is applied to the pressure receiving surface 3A of the diaphragm 3 and the diaphragm 3 is bent according to the pressure difference between the pressures applied to both surfaces of the diaphragm 3, the semiconductor chip 1d is distorted via the supporting members 2a to 2e and a stress is generated mainly in the thin-walled portion 1C. The resistors R1 to R4 constituting the strain gauge (bridge circuit) are formed in the region in which this tensile stress is generated.

Figure 35:
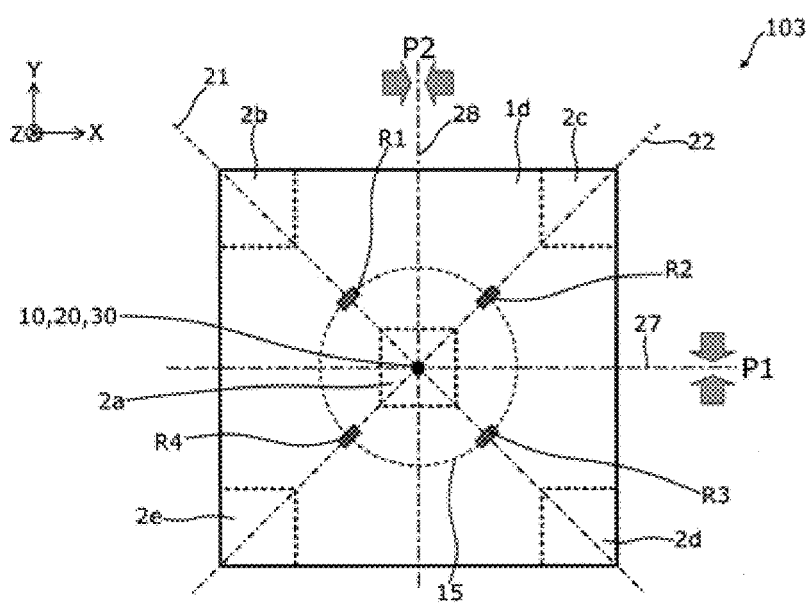
FIG. 35 illustrates an example of disposing resistors on the semiconductor chip in the pressure sensor according to embodiment 4.

FIG. 35 illustrates an example of disposing the resistors R1 to R4 on the semiconductor chip 1d in the pressure sensor 103 according to embodiment 4.

As illustrated in FIG. 35, the resistors R1 to R4 are formed in the straight lines 21 and 22 in plan view in the semiconductor chip 1d. Specifically, in the semiconductor chip 1d, the resistor R1 is formed in the straight line 21 in the region between the coupling surface of the supporting member 2a and the coupling surface of the supporting member 2b, the resistor R2 is formed in the straight line 22 in the region between the coupling surface of the supporting member 2a and the coupling surface of the supporting member 2c, the resistor R3 is formed in the straight line 21 in the region between the coupling surface of the supporting member 2a and the coupling surface of the supporting member 2d, and the resistor R4 is formed in the straight line 22 in the region between the coupling surface of the supporting member 2a and the coupling surface of the supporting member 2e.

The resistors R1 to R4 extend in the same direction. For example, the resistors R1 to R4 extend in the direction parallel to the straight line 22.

In addition, the resistors R1 to R4 are disposed equidistantly (within a deviation of, for example, plus or minus 10 percent) from the center 20 of the supporting member 2a. For example, the resistors R1 to R4 are formed in the circumference of the circle 15 having the same center as the semiconductor chip 1d in plan view. The circle 15 preferably has a diameter so the circle 15 fits within the thin-walled portion 1C.

Figure 36:
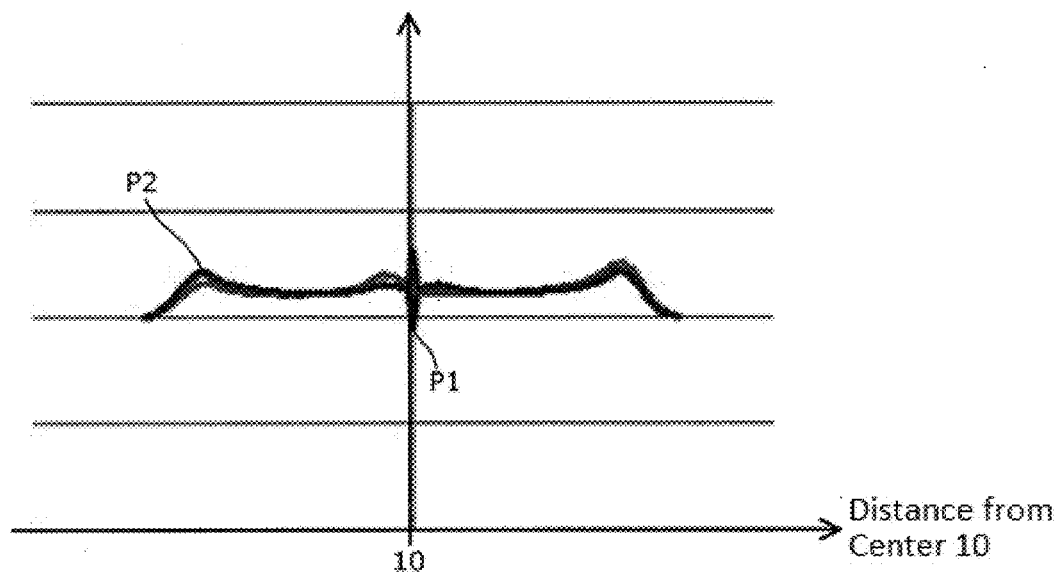
FIG. 36 illustrates the result of simulation of a sensor output from the pressure sensor according to embodiment 4.

FIG. 36 illustrates the result of simulation of an output signal of the bridge circuit 16 of the pressure sensor 103 using the FEM when the position of the nut 52 for fixing the clamp 50 is changed.

In FIG. 36, the horizontal axis represents the distance from the center 10 of the semiconductor chip 1d and the vertical axis represents the magnitude of the output signal (|Va−Vb|) of the bridge circuit 16 of the pressure sensor 103. In FIG. 36, reference numeral P1 represents the stress distribution of the semiconductor chip 1d when the nut 52 of the clamp 50 is fixed at position P1 in a straight line 27 illustrated in FIG. 35 and reference numeral P2 represents the stress distribution of the semiconductor chip 1d when the nut 52 of the clamp 50 is fixed at position P2 in a straight line 28 illustrated in FIG. 35.

In the pressure sensor 103 according to embodiment 4, the resistors R1 to R4 are formed in the region on the semiconductor chip 1d in which the displacement in the Z axis direction is reversed when the clamp 50 is tightened by the nut 52 as in the pressure sensor 100 according to embodiment 1, fluctuations in the resistance ratio between the resistor R1 and the resistor R4 and fluctuations in the resistance ratio between the resistor R2 and the resistor R3 when the nut 52 of the clamp 50 is tightened can be suppressed. As illustrated in FIG. 36, this can suppress the shift amount of the zero point of a sensor output (output signal |Va−Vb| of the bridge circuit 16) of the pressure sensor 103 when the nut 52 of the clamp 50 is tightened and also suppress variations in the above shift amount caused by the differences in the tightening position of the nut 52 of the clamp 50.

In particular, if the resistor R1 and the resistor R4 extend in the same direction and the resistor R2 and the resistor R3 extend in the same direction, the shift amount of the zero point of a sensor output of the pressure sensor 103 when the nut 52 of the clamp 50 is tightened can be further suppressed and variations in the shift amount can be further suppressed as in the pressure sensor 100 according to embodiment 1.

In addition, if the resistors R1 to R4 are formed equidistantly (for example, in the circumference of the circle 15) from the center 30 of the diaphragm 3 in plan view, the shift amount of the zero point of a sensor output of the pressure sensor 103 when the nut 52 of the clamp 50 is tightened can be further suppressed and variations in the above shift amount can be further suppressed as in the pressure sensor 100 according to embodiment 1.

In addition, the sensor sensitivity of the pressure sensor 103 with respect to the pressure applied to the pressure receiving surface 3A of the diaphragm 3 can be further improved by forming the resistors R1 to R4 in the regions corresponding to the thin-walled portion 1C of the semiconductor chip 1d in plan view.

Although the invention implemented by the inventors and the like has been described above specifically based on the embodiments, the invention is not limited to the embodiments and it will be appreciated that various modifications can be made without departing from the scope of the invention.

Figure 37:
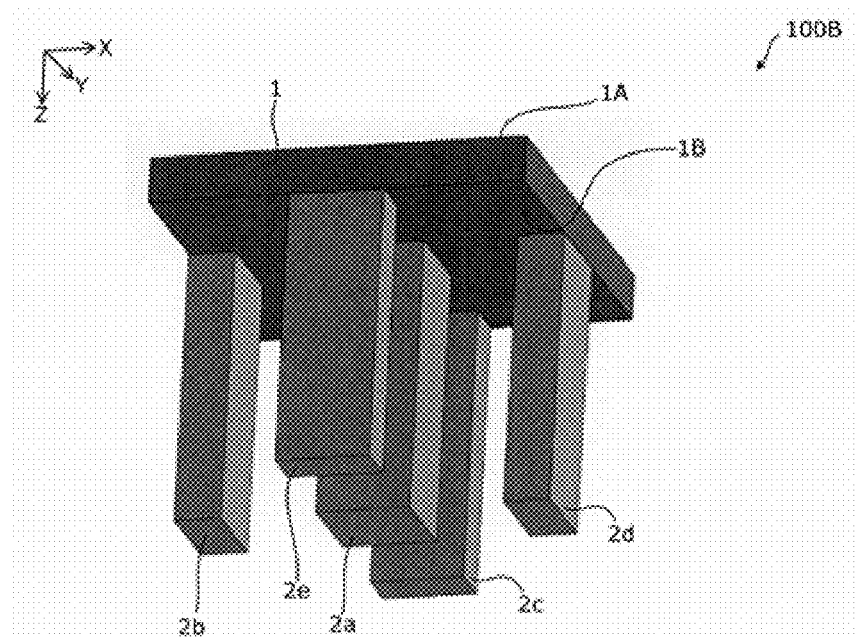
FIG. 37 is a perspective view illustrating a semiconductor chip of another pressure sensor according to embodiment 1 seen from a back surface.

For example, although the thin-walled portion 1C is formed on the back surface 1B of the semiconductor chip in embodiments 1 to 4, as long as sufficient sensor sensitivity can be obtained as the pressure sensor, the thickness between the principal surface 1A and the back surface 1B may be uniform without forming the thin-walled portion 1C as in a pressure sensor 100B illustrated in FIG. 37.

Figure 38:
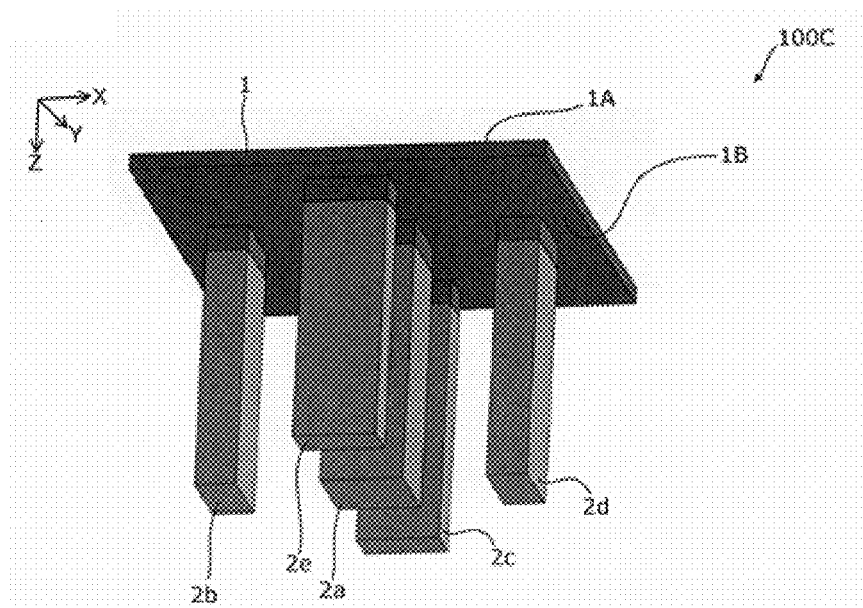
FIG. 38 is a perspective view illustrating another semiconductor chip of the other pressure sensor according to embodiment 1 seen from a back surface.

In addition, although the supporting members 2b to 2e are coupled to the back surface 1B of the semiconductor chip so that the side surfaces of the supporting members 2b to 2e are flush with the side surfaces of the semiconductor chip in embodiments 1 to 4, the supporting members 2b to 2e may be coupled to positions inward of the side surfaces of the semiconductor chip 1 as in a pressure sensor 100C illustrated in FIG. 38. For example, the supporting members 2b to 2e may be coupled to positions closer to the center 10 of the semiconductor chip 1 than in the pressure sensor 100 in FIG. 4.

Figure 39:
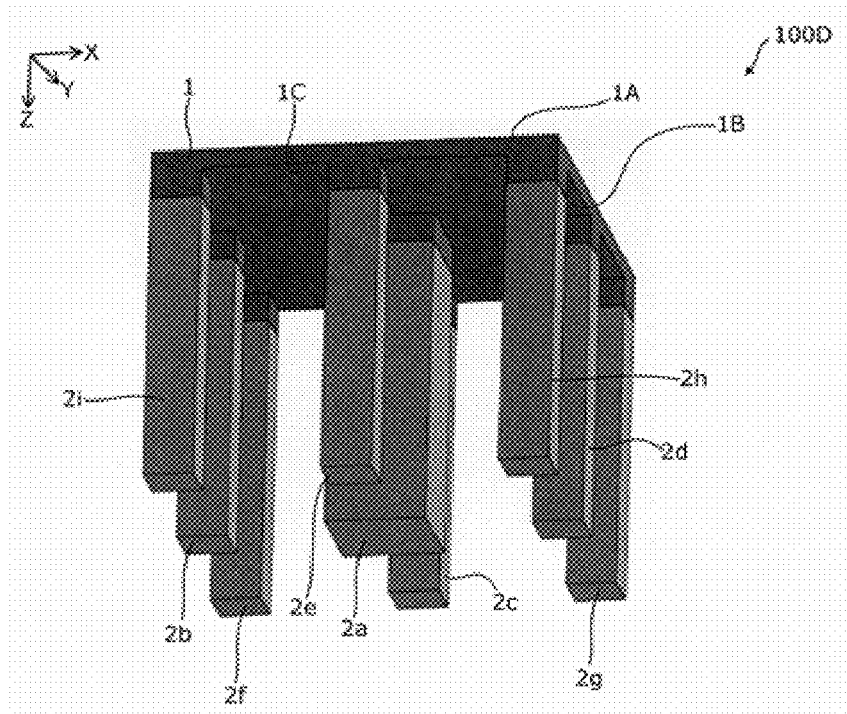
FIG. 39 is a perspective view illustrating yet another semiconductor chip of the other pressure sensor according to embodiment 1 seen from a back surface.
Figure 40:
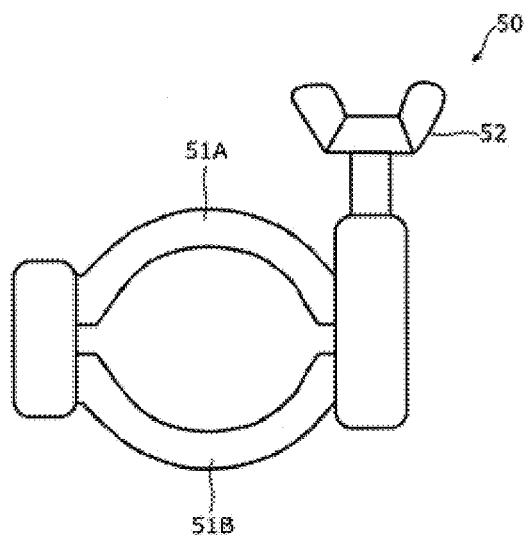
FIG. 40 illustrates the planar structure of a clamp for connecting a pressure sensor to a pipe.
Figure 41:
FIG. 41 illustrates a connection structure for a pressure sensor and a pipe via a clamp.
Figure 41:
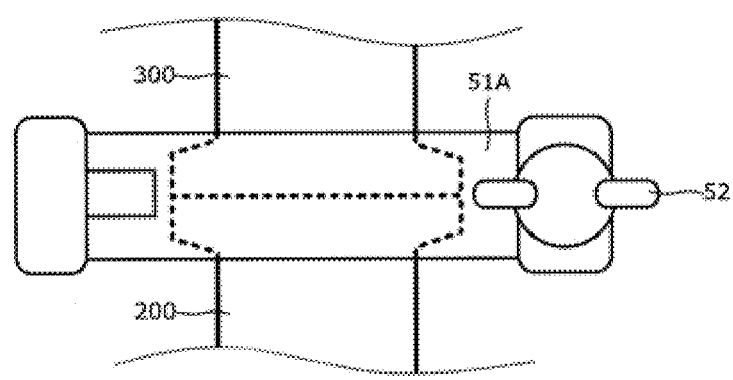

In addition, although the four supporting members 2b to 2e are included as the second structural bodies in embodiments 1, 2, and 4, the number of second structural bodies are not limited to four as long as at least one second structural body is disposed in each of the straight lines 21 and 22. For example, in FIGS. 6 and 18, when resistors constituting the strain gauge are not formed in the regions between the supporting members 2d and 2e and the supporting member 2a as the first structural body, the supporting members 2d and 2e may be removed. Alternatively, as in a pressure sensor 100D illustrated in FIG. 39, the number of supporting members as the second structural bodies may be five or more (e.g., 2b to 2i).

In addition, although the supporting members 2a to 2e are rectangular column in embodiments 1 to 4, they may be cylindrical columns.

In addition, although the resistor R1 and the resistor R4 extend in the same direction in the above embodiments, even when the resistor R1 and the resistor R4 do not extend in the same direction, as long as the direction in which the resistor R1 extends is not orthogonal to the direction in which the resistor R4 extends, the effect of reducing the shift amount of the zero point of a sensor output and variations in the shift amount can be expected. This is also true for the resistor R2 and the resistor R3.

In addition, in embodiments 1 to 4, the diameter of the circle 15 is not limited to that illustrated in FIG. 6 or the like and it will be appreciated that the diameter may be changed depending on the requested performance or the like.

DESCRIPTION OF REFERENCE NUMERALS AND SIGNS 100, 100A, 100B, 100C, 100D, 101, 101A, 102, 102A, 103, 103A: pressure sensor; 1, 1a, 1b, 1c, 1d: semiconductor chip; 1A: principal surface of semiconductor chip; 1B: back surface of semiconductor chip; 1C: thin-walled portion; 10: center of semiconductor chip; 2a, 2b, 2c, 2d, 2e, 2f, 2g, 2h, 2i: supporting member; 20: center of supporting member 2a; 3: diaphragm; 3A: pressure receiving surface; 3B: supporting surface; 12, 13: side; 30: center of diaphragm, 4: housing, 4A: end portion of housing, 4B: inner wall of housing, R1 to R4: resistor, 15: circle, 21, 22: straight line

The invention claimed is:
1. A pressure sensor comprising:
a diaphragm having a first principal surface receiving a pressure of a measurement target fluid and a second principal surface opposite to the first principal surface;
a semiconductor chip having a plurality of resistors on one surface thereof, the resistors being included in a strain gauge;
a first structural body having one end coupled to a center of the second principal surface of the diaphragm and another end coupled to another surface of the semiconductor chip; and
at least two second structural bodies having one ends coupled to respective deformable regions of the second principal surface and other ends coupled to the other surface of the semiconductor chip, the at least two second structural bodies being disposed in two straight lines that pass through the center of the second principal surface of the diaphragm and are orthogonal to each other in plan view, the at least two second structural bodies being disposed separately from the first structural body,
wherein the resistors are formed in regions between the first structural body and the second structural bodies in plan view.

2. The pressure sensor according to claim 1,
wherein the semiconductor chip is formed in a square in plan view,
the other end of the first structural body is coupled to a center of the other surface of the semiconductor chip, and
each of the other ends of the second structural bodies is coupled to the other surface of the semiconductor chip along each of sides of the other surface of the semiconductor chip.

3. A pressure sensor comprising:
a diaphragm having a first principal surface receiving a pressure of a measurement target fluid and a second principal surface opposite to the first principal surface;
a semiconductor chip having a plurality of resistors on one surface thereof, the resistors being included in a strain gauge;
a first structural body having one end coupled to a center of the second principal surface of the diaphragm and another end coupled to another surface of the semiconductor chip; and
at least two second structural bodies having one ends coupled to the second principal surface and other ends coupled to the other surface of the semiconductor chip, the at least two second structural bodies being disposed in two straight lines that pass through the center of the second principal surface of the diaphragm and are orthogonal to each other in plan view, the at least two second structural bodies being disposed separately from the first structural body,
wherein the resistors are formed in regions between the first structural body and the second structural bodies in plan view,
the other end of the first structural body is coupled to a center of the other surface of the semiconductor chip,
each of the other ends of the second structural bodies is coupled to the other surface of the semiconductor chip along each of sides of the other surface of the semiconductor chip,
the plurality of resistors are included in a bridge circuit,
a first resistor and a second resistor included in one of two pairs of resistors connected in parallel between two output terminals of the bridge circuit are formed in a region between a coupling surface of one of the second structural bodies disposed in one of the two straight lines and a coupling surface of the first structural body in plan view in the semiconductor chip and a third resistor and a fourth resistor included in another of the two pairs of resistors are formed in a region between a coupling surface of another of the second structural bodies disposed in the other of the two straight lines and the coupling surface of the first structural body in plan view in the semiconductor chip,
the first resistor and the fourth resistor extend in a same direction in plan view, and
the second resistor and the third resistor extend in another same direction in plan view.

4. The pressure sensor according to claim 3,
wherein the same direction in which the first resistor and the fourth resistor extend is orthogonal to the other same direction in which the second resistor and the third resistor extend in plan view.

5. A pressure sensor comprising:
a diaphragm having a first principal surface receiving a pressure of a measurement target fluid and a second principal surface opposite to the first principal surface;

a semiconductor chip having a plurality of resistors on one surface thereof the resistors being included in a strain gauge;

a first structural body having one end coupled to a center of the second principal surface of the diaphragm and another end coupled to another surface of the semiconductor chip; and at least two second structural bodies having one ends coupled to the second principal surface and other ends coupled to the other surface of the semiconductor chip, the at least two second structural bodies being disposed in two straight lines that pass through the center of the second principal surface of the diaphragm and are orthogonal to each other in plan view, the at least two second structural bodies being disposed separately from the first structural body, wherein the resistors are formed in regions between the first structural body and the second structural bodies in plan view, the other end of the first structural body is coupled to a center of the other surface of the semiconductor chip, each of the other ends of the second structural bodies is coupled to the other surface of the semiconductor chip along each of sides of the other surface of the semiconductor chip, the plurality of resistors include four resistors constituting a bridge circuit, and the four resistors extend in a same direction in plan view and each of the four resistors is formed in a region between a coupling surface of the first structural body and a coupling surface of each of the second structural bodies in the semiconductor chip.

6. The pressure sensor according to claim 1,
wherein the semiconductor chip is formed in a cross in plan view, the other end of the first structural body is coupled to a center of the other surface of the semiconductor chip, and each of the other ends of the second structural bodies is coupled to each of four arms on the other surface of the semiconductor chip.

7. The pressure sensor according to claim 6,
wherein the plurality of resistors are included in a bridge circuit, a first resistor and a second resistor included in one of two pairs of resistors connected in parallel between two output terminals of the bridge circuit are formed in a region between a coupling surface of one of the second structural bodies disposed in one of the two straight lines and a coupling surface of the first structural body in plan view in the semiconductor chip and a third resistor and a fourth resistor included in another of the two pairs of resistors are formed in a region between a coupling surface of another of the second structural bodies disposed in the other of the two straight lines and the coupling surface of the first structural body in plan view in the semiconductor chip, the first resistor and the fourth resistor extend in a same direction in plan view, and the second resistor and the third resistor extend in another same direction in plan view.

8. The pressure sensor according to claim 7,
wherein the same direction in which the first resistor and the fourth resistor extend is orthogonal to the other same direction in which the second resistor and the third resistor extend in plan view.

9. The pressure sensor according to claim 6,
wherein the plurality of resistors include four resistors constituting a bridge circuit, and the four resistors extend in a same direction in plan view and each of the four resistors is formed in a region between a coupling surface of the first structural body and a coupling surface of each of the second structural bodies in the semiconductor chip.

10. The pressure sensor according to claim 1,
wherein the at least two second structural bodies are two second structural bodies, the semiconductor chip is formed in a polygon in plan view, the other end of the first structural body is coupled to a region including one corner of the other surface of the semiconductor chip, the other end of one of the second structural bodies is coupled along one of two sides forming the one corner of the other surface of the semiconductor chip, the other end of the other of the second structural bodies is coupled along another of the two sides forming the one corner of the other surface of the semiconductor chip, the plurality of resistors are included in a bridge circuit, a first resistor and a second resistor included in one of two pairs of resistors connected in parallel between two output terminals of the bridge circuit are formed in a region between a coupling surface of the first structural body and a coupling surface of the one of the second structural bodies in plan view in the semiconductor chip and a third resistor and a fourth resistor included in another of the two pairs of resistors are formed in a region between the coupling surface of the first structural body and the coupling surface of the other of the second structural bodies in plan view in the semiconductor chip, the first resistor and the fourth resistor extend in a same direction in plan view, and the second resistor and the third resistor extend in another same direction in plan view.

11. The pressure sensor according to claim 10,
wherein the same direction in which the first resistor and the fourth resistor extend is orthogonal to the other same direction in which the second resistor and the third resistor extend in plan view.

12. The pressure sensor according to claim 10,
wherein an inner angle of one corner to which the first structural body and the second structural bodies are not coupled is larger than 180 degrees in plan view in the semiconductor chip.

13. The pressure sensor according to claim 1,
wherein the semiconductor chip is formed in a square in plan view, the plurality of resistors includes four resistors constituting a bridge circuit, the other end of the first structural body is coupled to a center of the other surface of the semiconductor chip, the other ends of the second structural bodies are coupled to four corners of the other surface of the semiconductor chip, and the four resistors extend in a same direction in plan view and each of the four resistors is formed in a region between a coupling surface of the first structural body and each of coupling surfaces of the second structural bodies in the semiconductor chip.

14. The pressure sensor according to claim 1,
wherein the plurality of resistors is disposed equidistantly from a center of the first structural body in plan view.

15. The pressure sensor according to claim 1,
wherein the semiconductor chip has a thin-walled portion thinner than a portion to which the first structural body and the second structural bodies are coupled, and
the plurality of resistors are formed in a region on the one surface of the semiconductor chip, the region corresponding to the thin-walled portion.

16. The pressure sensor according to claim 2,
wherein the plurality of resistors are included in a bridge circuit,
a first resistor and a second resistor included in one of two pairs of resistors connected in parallel between two output terminals of the bridge circuit are formed in a region between a coupling surface of one of the second structural bodies disposed in one of the two straight lines and a coupling surface of the first structural body in plan view in the semiconductor chip and a third resistor and a fourth resistor included in another of the two pairs of resistors are formed in a region between a coupling surface of another of the second structural bodies disposed in the other of the two straight lines and the coupling surface of the first structural body in plan view in the semiconductor chip,
the first resistor and the fourth resistor extend in a same direction in plan view, and
the second resistor and the third resistor extend in another same direction in plan view.

17. The pressure sensor according to claim 16,
wherein the same direction in which the first resistor and the fourth resistor extend is orthogonal to the other same direction in which the second resistor and the third resistor extend in plan view.

18. The pressure sensor according to claim 1,
wherein the plurality of resistors include four resistors constituting a bridge circuit, and
the four resistors extend in a same direction in plan view and each of the four resistors is formed in a region between a coupling surface of the first structural body and a coupling surface of each of the second structural bodies in the semiconductor chip.

* * * * *